United States Patent [19]

Rich et al.

[11] 4,439,015
[45] Mar. 27, 1984

[54] DISUBSTITUTED ETHANES

[75] Inventors: Roland Rich, Hésingue, France; Alois Villiger, Basel; Erich Widmer, Münchenstein, both of Switzerland

[73] Assignee: Hoffmann-La Roche Inc., Nutley, N.J.

[21] Appl. No.: 341,926

[22] Filed: Jan. 22, 1982

[30] Foreign Application Priority Data

Jan. 30, 1981 [CH] Switzerland ............ 619/81
Oct. 13, 1981 [CH] Switzerland ........... 6545/81

[51] Int. Cl.³ ................... G02F 1/13; C09K 3/34
[52] U.S. Cl. ................. 350/350 R; 252/299.5; 252/299.6; 252/299.61; 252/299.62; 252/299.63; 560/8; 560/138; 568/329; 568/631; 585/20; 585/25
[58] Field of Search ......... 252/299.5, 299.61, 299.62, 252/299.63, 299.6; 585/20, 25; 568/631, 329; 560/8, 138; 260/460; 350/350

[56] References Cited

U.S. PATENT DOCUMENTS

| | | | |
|---|---|---|---|
| 4,035,056 | 7/1977 | Coates et al. | 252/299.6 |
| 4,062,798 | 12/1977 | Boller et al. | 252/299.61 |
| 4,149,413 | 4/1979 | Gray et al. | 252/299.67 |
| 4,180,475 | 12/1979 | Schadt et al. | 252/299.5 |
| 4,198,130 | 4/1980 | Boller et al. | 252/299.5 |
| 4,222,888 | 9/1980 | Dubois et al. | 252/299.64 |
| 4,261,651 | 4/1981 | Gray et al. | 350/350 R |
| 4,357,078 | 11/1982 | Carr et al. | 252/299.63 |
| 4,361,494 | 11/1982 | Osman et al. | 252/299.63 |

FOREIGN PATENT DOCUMENTS

| | | | |
|---|---|---|---|
| 56113 | 7/1982 | European Pat. Off. | 252/299.63 |
| 58512 | 8/1982 | European Pat. Off. | 252/299.63 |
| 2922236 | 6/1979 | Fed. Rep. of Germany | 252/299.63 |
| 2949080 | 6/1981 | Fed. Rep. of Germany | 252/299.62 |
| 3200967 | 9/1982 | Fed. Rep. of Germany | 252/299.63 |
| 57-163324 | 10/1982 | Japan | 252/299.63 |
| 58-8022 | 1/1983 | Japan | 252/299.63 |
| 58-10529 | 1/1983 | Japan | 252/299.63 |
| 2082179 | 3/1982 | United Kingdom | 252/299.62 |
| 2084576 | 4/1982 | United Kingdom | 252/299.62 |
| 2090593 | 7/1982 | United Kingdom | 252/299.62 |

OTHER PUBLICATIONS

Demus, D., Nonemissive Electrooptic Displays, pp. 83–119 (1975).
Praefcke, K. et al., Chemiker-Zeitunl, vol. 104, No. 9, pp. 269–271 (1980).
Gray, G. W., "Relationship Between Chemical Structure and Properties for Low Molecular Weight Liquid Crystals," Presented at Santa Margherita Ligure, Italy (Jun. 1981).
Gray, Lecture on "Relationship Between Chemical Structure and Properties for Low Molecular Weight Liquid Crystals' at Santa Margherita Ligure, Italy (Jun., 1981) (handwritten copies of the slides).
Gray et al., Mol. Cry. Liq. Cry. 53, 147–166 (1979).

Primary Examiner—Teddy S. Gron
Attorney, Agent, or Firm—Jon S. Saxe; Bernard S. Leon; George W. Johnston

[57] ABSTRACT

Disubstituted ethanes of the formula

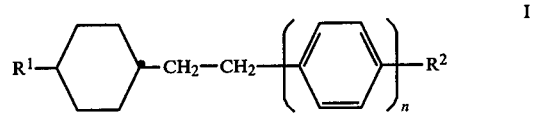

wherein $R^2$ is $-R^3$, $-OR^3$, $-CO-R^3$, $-CO-OR^3$ or $O-CO-R^3$, $R^1$ and $R^3$ each are straight-chain alkyl of 1 to 12 carbon atoms and n is 1 or 2, are described. Liquid crystalline mixtures comprising Compound I as well as their use in electro-optical devices also are disclosed.

20 Claims, No Drawings

DISUBSTITUTED ETHANES

BACKGROUND OF THE INVENTION

1. Field of the Invention

This invention relates to liquid crystalline compounds and mixtures.

2. Description of the State of the Art

In an electric field, the molecules of liquid crystalline compounds and mixtures which possess a positive anisotropy of the dielectric constants (i.e. $\epsilon_\| > \epsilon_\perp$) are oriented with their longitudinal axes (i.e., largest dielectric constant) parallel to the field direction. $\epsilon_\|$ signifies the dielectric constant along the longitudinal axis of the molecule and $\epsilon_\perp$ signifies the dielectric constant perpendicular thereto.

This dielectric field effect is utilized in the interaction between the liquid crystalline molecules and guest molecules (guest-host interaction) described by J. H. Heilmeier and L. A. Zanoni [Applied Physics Letter 13, 91 (1968)]. Another application of the dielectric field effect is the electro-optical rotation cell discovered by M. Schadt and W. Helfrich [Applied Physics Letters 18 (1971)]. A further example is the Kerr cell described in Molecular Crystals and Liquid Crystals 17, 355 (1972).

The electro-optical rotation cell includes a condenser-like structure having transparent electrode plates, the dielectric of which is formed from nematic liquid crystal material with $\epsilon_\| > \epsilon_\perp$. The longitudinal axes of the liquid crystal molecules are arranged in twisted or helical form between the plates in the fieldless state. The twisting structure is determined by the given wall orientation of the molecules. After applying an electric potential to the condenser plates, the molecules adjust themselves with their longitudinal axes in the field direction, i.e., perpendicular to the surface of the plates, so that linear polarized light no longer rotates in the dielectric (i.e. the liquid crystal is uniaxially perpendicular to the surface of the plates). After removing the electric potential, the molecules return to their prior orientation. This reversible effect on the molecules can be used to electrically control the optical transmissivity of the condenser. To achieve an optimal transition between these two orientations, the threshold potential of the compounds or mixtures can be adjusted to the driving potential of the rotation cell. The driving potential of such a "light rotation cell" is dependent on the battery potential and the control circuit used. It thus becomes desirable to utilize liquid crystalline mixtures having low threshold potentials.

Further, a mixture of nematic liquid crystals with positive anisotropy and cholesteric substances (or generally, soluble, optically active substances provided the total mixture remains liquid crystalline) undergoes a phase transition upon application of an electric field. This phase change effect is reversible and makes it possible to have high switching speeds of electro-optical devices which operate with such mixtures. By selecting the concentration of cholesteric additives in the liquid crystal mixture, one attempts to improve the electro-optical properties of rotational cells.

It also is known that liquid crystalline mixtures with low viscosities have short response times.

We have invented liquid crystalline compounds and mixtures which advantageously possess low viscosities, good chemical stability, large mesophase ranges and high UV-stability.

SUMMARY OF THE INVENTION

The invention relates to disubstituted ethanes of the formula

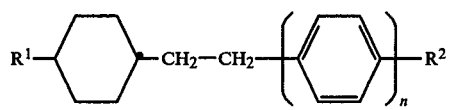

wherein $R^2$ is —$R^3$, —$OR^3$, —CO—$R^3$, —CO—$OR^3$ or —O—CO—$R^3$, $R^1$ and $R^3$ each are straight-chain alkyl of 1 to 12 carbon atoms and n is 1 or 2.

The compounds are useful in liquid crystalline mixtures for electro-optical devices.

DETAILED DESCRIPTION OF THE INVENTION

The present invention relates to (trans-4-alkylcyclohexyl)ethanes of the formula

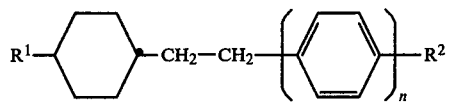

wherein $R^2$ is —$R^3$, —$OR^3$, —CO—$R^3$, —CO—$OR^3$ or —O—CO—$R^3$, $R^1$ and $R^3$ each are straight-chain alkyl of 1 to 12 carbon atoms and n is 1 or 2.

The compounds of formula I are liquid crystalline compounds with surprisingly low viscosities. When n is 1, the compounds of formula I have especially low viscosities and relatively low melting points. Moreover, the melting points often are supercoolable. Accordingly, these compounds are suitable particularly for lowering the viscosities and the melting points of liquid crystalline mixtures. On the other hand, the compounds of formula I in which n is 2 exhibit large mesophase ranges. These compounds are suitable particularly for increasing the clearing point of low viscosity mixtures, whereby the viscosity is not increased or is increased only insignificantly.

The inventive compounds are further distinguished by having a good chemical stability, by being colorless and by having a high UV-stability.

Unless otherwise stated, "alkyl" denotes a straight-chain alkyl group of 1 to 12 carbon atoms or a branched-chain alkyl group of 1 to 12 carbon atoms. Exemplary straight-chain alkyl groups are methyl, ethyl, propyl, butyl, pentyl, hexyl, heptyl, octyl, nonyl, decyl, undecyl and dodecyl. Exemplary branched-chain alkyl groups are isopropyl, isobutyl, sec-butyl, 1-methylbutyl, 2-methylbutyl 3-methylpentyl, 4-methylhexyl and isopentyl. Lower alkyl denotes straight-chain and branched-chain alkyl groups of 1 to 5 carbon atoms.

The terms "alkoxy" (—OR), "alkanoyl" (—CO—R), "alkoxycarbonyl" (—CO—OR), "alkylthiocarbonyl" (—CO—SR) and "alkanoyloxy" (—O—CO—R) denote moieties in which its "alkyl" portion is as defined previously. In particular, straight-chain alkoxy groups denote moieties having a straight-chain alkyl portion as previously defined.

The term "aromatic" means a phenyl ring.

The term "readily cleavable alcohol protecting group" includes those alcohol protecting groups which can be cleaved off under conditions which do not affect an alkoxy group.

The term "halogen" denotes chlorine, bromine or iodine.

In a preferred aspect of the invention, the compounds of formula I include those in which $R^2$ is —$R^3$, —$OR^3$ or —CO—$OR^3$. Those compounds of formula I in which $R^2$ is alkyl —$R^3$ or an alkoxy —$OR^3$ where $R^3$ is as above especially are preferred. Furthermore, the compound of formula I in which n is 1 are preferred. According to the invention, preferred $R^3$ groups are straight-chain alkyl of 1 to 10 carbon atoms and especially straight-chain alkyl of 1 to 7 carbon atoms. Further, the $R^1$ groups with 2 to 10 carbon atoms are preferred and those having 3 to 7 carbon atoms especially are preferred.

The following are preferred compounds of formula I:

2-(Trans-4-propylcyclohexyl)-1-(p-propylphenyl)ethane,
2-(trans-4-propylcyclohexyl)-1-(p-pentylphenyl)ethane,
2-(trans-4-propylcyclohexyl)-1-(p-hexylphenyl)ethane,
2-(trans-4-butylcyclohexyl)-1-(p-propylphenyl)ethane,
2-(trans-4-butylcyclohexyl)-1-(p-pentylphenyl)ethane,
2-(trans-4-pentylcyclohexyl)-1-(p-propylphenyl)ethane,
2-(trans-4-pentylcyclohexyl)-1-(p-pentylphenyl)ethane,
2-(trans-4-pentylcyclohexyl)-1-(p-hexylphenyl)ethane,
2-(trans-4-heptylcyclohexyl)-1-(p-propylphenyl)ethane,
2-(trans-4-heptylcyclohexyl)-1-(p-butylphenyl)ethane,
2-(trans-4-heptylcyclohexyl)-1-(p-pentylphenyl)ethane,
2-(trans-4-ethylcyclohexyl)-1-(p-ethoxyphenyl)ethane,
2-(trans-4-ethylcyclohexyl)-1-(p-butyloxyphenyl)ethane,
2-(trans-4-ethylcyclohexyl)-1-(p-hexyloxyphenyl)ethane,
2-(trans-4-propylcyclohexyl)-1-(p-methoxyphenyl)ethane,
2-(trans-4-propylcyclohexyl)-1-(p-ethoxyphenyl)ethane,
2-(trans-4-propylcyclohexyl)-1-(p-propyloxyphenyl)ethane,
2-(trans-4-propylcyclohexyl)-1-(p-butyloxyphenyl)ethane,
2-(trans-4-butylcyclohexyl)-1-(p-methoxyphenyl)ethane,
2-(trans-4-butylcyclohexyl)-1-(p-ethoxyphenyl)ethane,
2-(trans-4-butylcyclohexyl)-1-(p-butyloxyphenyl)ethane,
2-(trans-4-pentylcyclohexyl)-1-(p-methoxyphenyl)ethane,
2-(trans-4-pentylcyclohexyl)-1-(p-ethoxyphenyl)ethane,
2-(trans-4-pentylcyclohexyl)-1-(p-propyloxyphenyl)ethane,
2-(trans-4-pentylcyclohexyl)-1-(p-butyloxyphenyl)ethane,
2-(trans-4-heptylcyclohexyl)-1-(p-methoxyphenyl)ethane,
2-(trans-4-heptycyclohexyl)-1-(p-ethoxyphenyl)ethane,
2-(trans-4-heptylcyclohexyl)-1-(p-butyloxyphenyl)ethane,
p-[2-(trans-4-propylcyclohexyl)-1-ethyl]phenylacetate,
p-[2-(trans-4-propylcyclohexyl)-1-ethyl]phenylbutyrate,
p-[2-(trans-4-butylcyclohexyl)-1-ethyl]phenylacetate,
p-[2-(trans-4-butylcyclohexyl)-1-ethyl]phenylbutyrate,
p-[2-(trans-4-pentylcyclohexyl)-1-ethyl]phenylacetate,
p-[2-(trans-4-pentylcyclohexyl)-1-ethyl]phenylbutyrate,
p-[2-(trans-4-heptylcyclohexyl)-1-ethyl]phenylacetate,
p-[2-(trans-4-ethylcyclohexyl)-1-ethyl]benzoic acid methyl ester,
p-[2-(trans-4-ethylcyclohexyl)-1-ethyl]benzoic acid ethyl ester,
p-[2-(trans-4-propylcyclohexyl)-1-ethyl]benzoic acid methyl ester,
p-[2-(trans-4-propylcyclohexyl)-1-ethyl]benzoic acid ethyl ester,
p-[2-(trans-4-propylcyclohexyl)-1-ethyl]benzoic acid propyl ester,
p-[2-(trans-4-butylcyclohexyl)-1-ethyl]benzoic acid methyl ester,
p-[2-(trans-4-butylcyclohexyl)-1-ethyl]benzoic acid ethyl ester,
p-[2-(trans-4-pentylcyclohexyl)-1-ethyl]benzoic acid methyl ester,
p-[2-(trans-4-pentylcyclohexyl)-1-ethyl]benzoic acid ethyl ester,
p-[2-(trans-4-hexylcyclohexyl)-1-ethyl]benzoic acid methyl ester,
p-[2-(trans-4-hexylcyclohexyl)-1-ethyl]benzoic acid ethyl ester,
p-[2-(trans-4-heptylcyclohexyl)-1-ethyl]benzoic acid methyl ester,
p-[2-(trans-4-heptylcyclohexyl)-1-ethyl]benzoic acid ethyl ester,
p-[2-(trans-4-propylcyclohexyl)-1-ethyl]propiophenone,
p-[2-(trans-4-propylcyclohexyl)-1-ethyl]valerophenone,
p-[2-(trans-4-pentylcyclohexyl)-1-ethyl]propiophenone,
p-[2-(trans-4-pentylcyclohexyl)-1-ethyl]valerophenone,
p-[2-(trans-4-pentylcyclohexyl)-1-ethyl]hexanophenone,
2-(trans-4-ethylcyclohexyl)-1-(4'-propyl-4-biphenylyl)ethane,
2-(trans-4-propylcyclohexyl)-1-(4'-ethyl-4-biphenylyl)ethane,
2-(trans-4-propylcyclohexyl)-1-(4'-propyl-4-biphenylyl)ethane,
2-(trans-4-propylcyclohexyl)-1-(4'-pentyl-4-biphenylyl)ethane,
2-(trans-4-pentylcyclohexyl)-1-(4'-ethyl-4-biphenylyl)ethane,
2-(trans-4-pentylcyclohexyl)-1-(4'-propyl-4-biphenylyl)ethane,
2-(trans-4-pentylcyclohexyl)-1-(4'-pentyl-4-biphenylyl)ethane,
2-(trans-4-ethylcyclohexyl)-1-(4'-butyloxy-4-biphenylyl)ethane,
2-(trans-4-propylcyclohexyl)-1-(4'-ethoxy-4-biphenylyl)ethane,
2-(trans-4-propylcyclohexyl)-1-(4'-butyloxy-4-biphenylyl)ethane,
2-(trans-4-pentylcyclohexyl)-1-(4'-ethoxy-4-biphenylyl)ethane,
2-(trans-4-pentylcyclohexyl)-1-(4'-butyloxy-4-biphenylyl)ethane,
4'-[2-(trans-4-propylcyclohexyl)-1-ethyl]-4-biphenylyl acetate,
4'-[2-(trans-4-propylcyclohexyl)-1-ethyl]-4-biphenylyl butyrate,
4'-[2-(trans-4-propylcyclohexyl)-1-ethyl]-4-biphenylyl carboxylic acid methyl ester,
4'-[2-(trans-4-propylcyclohexyl)-1-ethyl]-4-biphenylyl carboxylic acid ethyl ester,
4'-[2-(trans-4-propylcyclohexyl)-1-ethyl]-4-biphenylyl carboxylic acid propyl ester, 4'-[2-(trans-4-pentylcyclohexyl)-1-ethyl]-4-biphenylyl-carboxylic acid methyl ester, 4'-[2-(trans-4-pentylcyclohexyl)-1-ethyl]-4-biphenylyl-carboxylic acid ethyl ester, and 2-(trans-4-propylcyclohexyl)-1-(4'-butyryl-4-biphenylyl)ethane.

In accordance with the invention, Compound I can be manufactured by reducing a compound of the formula

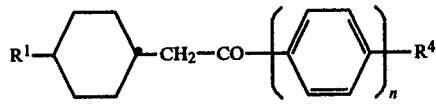

wherein $R^4$ is hydrogen, hydroxy, halogen, $-R^3$ or $-OR^3$ and $R^1$, $R^3$ and n are as above,
and acylating the resulting compound of the formula

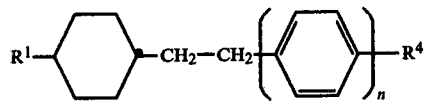

wherein $R^1$, $R^4$ and n are as above,
when $R^4$ is hydrogen, or, when $R^4$ is hydroxy, esterifying the resulting Compound III with a carboxylic acid of the formula $R^3$COOH or a reactive derivative thereof or, when $R^4$ is halogen, reacting the resulting Compound III with magnesium and subsequently with carbon dioxide, hydrolyzing the resulting carboxylate and esterifying the resulting acid or a reactive derivative thereof with an alcohol of the formula $R^3$OH where $R^3$ is as above.

The reduction of Compound II can be carried out according to known methods. Preferably, Compound II is reacted with hydrazine in the presence of a base (e.g. potassium hydroxide, sodium ethylate, potassium t-butylate and the like) in an inert organic solvent such as dimethyl sulphoxide or an alcohol (e.g. ethanol, diethyleneglycol, triethyleneglycol and the like). Subsequently, the resulting hydrazone is decomposed. In general, the resulting hydrazine is decomposed only at an elevated temperature (e.g. at about 200° C.). If, however, dimethyl sulphoxide is used as the solvent, then the decomposition frequently already occurs at room temperature (about 23° C.).

In a preferred embodiment, the reduction of Compound II is carried out according to the Huang-Minlon process. More particularly, one heats the ketone under reflux in a high-boiling solvent which is miscible with water (e.g. diethyleneglycol or triethyleneglycol) together with hydrazine hydrate and potassium hydroxide, subsequently distills off the water until the hydrazone decomposes and one continues the boiling under reflux until the reduction is complete.

A Clemmensen reduction is an additionally preferred method for reducing Compound II. In accordance with this method, the ketone is warmed with amalgamated zinc and hydrochloric acid. If desired, an organic solvent such as ethanol, acetic acid, dioxan, toluene and the like can be added.

Furthermore, Compound II in which $R^4$ is hydrogen or alkyl can be reduced by catalytic hydrogenation. This hydrogenation can be carried out with conventional hydrogenation catalysts (e.g. palladium, platinum, Raney-nickel and the like), if desired supported on an inert carrier material (e.g. carbon). Palladium and platinum are the preferred catalysts. The solvent can be any inert organic solvent such as a saturated alcohol, an ether, an ester, a carboxylic acid, a hydrocarbon and the like (e.g. ethanol, dioxan, ethyl acetate, glacial acetic acid or hexane). In this catalytic hydrogenation, the temperature and pressure are not critical. A temperature between about room temperature and about the boiling point of the mixture and a pressure of about 1 to about 5 atmospheres conveniently are used.

The reduction of Compound II in which $R^4$ is hydrogen or alkyl also can be carried out by reacting said compound with an alkanethiol or alkanedithiol (e.g. ethanethiol, 1, 3-propanedithiol, ethanedithiol and the like) and subsequently cleaving the resulting thioketal by catalytic hydrogenation with Raney-nickel. Preferred thiols are 1, 3-propanedithiol and especially ethanedithiol, which give cyclic thioketals. Illustratively, the formation of the thioketal can be catalyzed with boron trifluoride etherate. Conveniently, the preparation of the thioketal and the hydrogenation are carried out in an inert organic solvent such as diethyl ether, dioxan, methylene chloride, chloroform and the like. When it is liquid, the thiol can also simultaneously serve as the solvent. The pressure and temperature are not critical; atmospheric pressure and about room temperature are conveniently used.

Compound II in which $R^4$ is $-R^3$ or $-OR^3$ where $R^3$ is as above is converted directly into corresponding Compound I by the foregoing reduction (i.e. the compounds of formula III in this case are end products). Compound II in which $R^4$ is hydrogen, hydroxy or halogen must, on the other hand, be reacted further after the reduction to Compound III.

The acylation of Compound III in which $R^4$ is hydrogen can be carried out by reaction with a carboxylic acid chloride, bromine or anhydride (preferably the corresponding carboxylic acid chloride) in the presence of a Lewis acid such as aluminium trichloride, tin tetrachloride, boron trifluoride and the like (preferably aluminium trichloride) according to known methods for the Friedel-Crafts acylation. The reaction is carried out in an inert organic solvent, for example carbon disulphide or a chlorinated hydrocarbon (preferably methylene chloride or chloroform). The reaction conveniently is carried out at a temperature between about 0° C. and about the reflux temperature of the reaction mixture. The pressure is not critical and the reaction is advantageously carried out at atmospheric pressure and about room temperature.

The esterification of Compound III in which $R^4$ is hydroxy with an alkanecarboxylic acid of the formula $R^3$COOH where $R^3$ is as above or a reactive derivative thereof (e.g. an anhydride or acid halide) can be carried out in a known manner. The esterification of an alcohol with a carboxylic acid conveniently is carried out in the presence of a catalytic amount of a strong acid (e.g. sulphuric acid or a hydrohalic acid), in the presence (or absence) of an inert organic solvent. The reaction can also be carried out in the presence of N,N'-dicyclohexylcarbodiimide and 4-(dimethylamino)pyridine. The preferred method, however, is to esterify the alcohol with an acid chloride. This esterification conveniently is carried out in an inert organic solvent (e.g. an ether such as diethyl ether or tetrahydrofuran, dimethylformamide, benzene, toluene, cyclohexane, carbon tetrachloride and the like).

To bind the hydrogen chloride which is liberated during the esterification, an acid-binding agent (e.g. tertiary amines, pyridines and the like) is conveniently used. The acid-binding agent preferably is used in large excess, so that it can simultaneously serve as the solvent. The temperature and pressure are not critical and this esterification is generally carried out at atmospheric pressure and a temperature between about room temperature and about the boiling point of the mixture. Compound III in which $R^4$ is hydroxy can be obtained (instead of from corresponding compounds of formula II) from Compound III in which $R^4$ is alkoxy according to known ether cleavage methods.

Compound III in which $R^4$ is halogen (preferaly bromine) can be converted in a known manner with magnesium into the corresponding Grignard compounds. The solvent conveniently used is an ether, preferably diethyl ether or tetrahydrofuran. The pressure and temperature of the reaction are not critical. The reaction is generally carried out at atmospheric pressure and a temperature between about 0° C. and about the reflux temperature of the reaction mixture, preferably at approximately room temperature.

The Grignard compounds obtained can be converted with carbon dioxide into corresponding carboxylates which can be subsequently hydrolyzed to carboxylic acids. The reaction with carbon dioxide conveniently is carried out by conducting carbon dioxide gas into the solution of the Grignard compound obtained as described earlier at about 0° C. or by pouring said solution onto dry-ice. The hydrolysis of the carboxylate can be carried out using a strong acid, preferably a dilute inorganic acid such as hydrohalic acid, sulphuric acid and the like.

The esterification of the resulting acids or the corresponding acid halides or anhydrides with an alkanol of the formula $R^3OH$ wherein $R^3$ is as above can be carried out in an analogous manner to the esterification described earlier. The acid halides and anhydrides can be prepared in a known manner. Illustratively, acid chlorides are obtained by reacting the acid with phosphorus trichloride, phosphorus pentachloride, thionyl chloride and the like. Acid anhydrides are obtained by reacting the acid with acetic anhydride, acetyl chloride, ethyl chloroformate and the like. Methyl esters can also be obtained by reacting the corresponding carboxylic acid with diazomethane in an inert organic solvent, preferably diethyl ether.

Starting materials of formula II can be prepared by acylating a compound of the formula

IV wherein $R^4$ and n are as above,
with an acid chloride derived from a compound of the formula

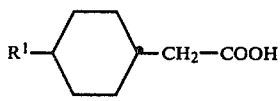

V wherein $R^1$ is as above.

This reaction can be carried out according to known methods for the Friedel-Crafts acylation (and especially in an analogous manner to the Friedel-Crafts acylation described earlier). Illustratively the acid chlorides can be prepared by heating the corresponding acids of formula V with thionyl chloride.

The compounds of formuas IV and V are known or can be prepared from known compounds by conventional techniques.

The present invention also concerns liquid crystalline mixtures.

Compound I preferably is used for manufacturing nematic and cholestric-type liquid crystalline mixtures with positive anisotropy of the dielectric constants ($\epsilon_\| > \epsilon_{195}$). The compounds of formula I thus are valuable especially as components of liquid crystalline mixtures. Most of such compounds exhibit liquid crystalline (nematic and/or smectic) properties.

The compounds of formula I can be mixed with other liquid crystalline and/or nonliquid crystalline substances to form liquid crystalline mixtures. Illustratively, such substances can be selected from classes of Schiff's bases, azobenzenes, azoxybenzenes, phenyl benzoates, cyclohexanecarboxylic acid phenyl esters, biphenyls, terphenyl, phenylcyclohexanes, cinnamic acid derivatives, phenyl pyrimidines, diphenylpyrimidines, phenyldioxanes, cyclohexylphenylpyrimidines and the like. Such substances are known to a person skilled in the art. See, e.g., German Offenlegungsschriften Nos. 2,306,738 (U.S. Pat. No. 3,927,064); 2,306,739 (U.S. Pat. No. 3,923,857); 2,429,093; 2,356,085 (U.S. Pat. No. 3,947,375); 2,636,684 (U.S. Pat. No. 4,130,502); 2,459,374 (U.S. Pat. No. 3,927,066); 2,547,737 (U.S. Pat. No. 3,997,536); 2,641,724 (U.S. Pat. No. 4,062,798); 2,708,276 (U.S. Pat. No. 4,180,475); 2,811,001 (U.S. Pat. No. 4,309,539 and 2,922,236 (U.S. Pat. No. 4,261,651); East German Patent Specification Nos. 139,852 and 139,867 and European Patent Application Publication No. 0014885 (U.S. Pat. No. 4,273,929). Many of such substances are available commercially.

In one aspect, the inventive mixtures include at least one compound of formula I and one or more liquid crystalline or nonliquid crystalline substances. On the other hand, the inventive mixture may only contain two or more compounds of formula I.

In addition to at least one compound of formula I, the inventive mixtures also can include hydrogenated naphthalenes of the formula

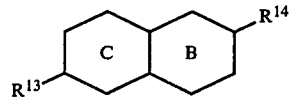

XXI wherein ring C is saturated; ring B is saturated or aromatic with the saturated ring B being trans-linked with ring C; $R^{13}$ is straight-chain alkyl or alkoxy of 1 to 11 carbon atoms; $R^{14}$ is cyano, straight-chain alkyl of 1 to 11 carbon atoms or an ester group of the formula

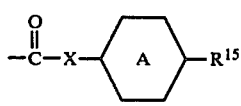

XXII or, when ring B is saturated, $R^{14}$ can also be straight-chain alkoxy of 1 to 11 carbon atoms; in ester XXII ring A is aromatic, X is oxygen or sulphur and $R^{15}$ is cyano or straight-chain alkyl or alkoxy of 1 to 10 carbon atoms, or ring A is a trans-1,4-disubstituted cyclohexane ring, X is oxygen and $R^{15}$ is cyano or straight-chain alkyl of 1 to 10 carbon atoms; with the proviso that the total number of carbon atoms in the alkyl and alkoxy groups present is at most 12;

and/or benzodioxanes of the formula

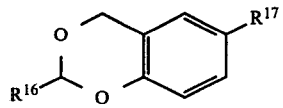   XXIII wherein $R^{16}$ is straight-chain alkyl of 1 to 11 carbon atoms; $R^{17}$ is cyano, straight-chain alkyl of 1 to 11 carbon atoms or ester XXII hereinbefore in which X, A and $R^{15}$ are as above; with the proviso that the total number of carbon atoms in the alkyl and alkoxy groups present is at most 12;

and/or trans-(4-alkylcyclohexyl)pyrimidines of the formula

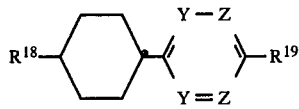   XXIV wherein Y is nitrogen and Z is =CH—, or Z is nitrogen and Y is =CH—; $R^{18}$ is alkyl and $R^{19}$ is cyano, alkyl, p-alkylphenyl or trans-4-alkylcyclohexyl; where each alkyl denotes either a straight-chain alkyl group of 1 to 12 carbon atoms or a branched-chain alkyl group of the formula $C_2H_5$—$CH(CH_3)$—$(CH_2)_m$—, m is 1, 2 or 3; with the proviso that the compound contains at most only one of said branched-chain alkyl group and with further proviso that the sum of the carbon atoms in all of the alkyl groups within the compound is at most 14;

and/or equatorially substituted trans-decalins of the formula

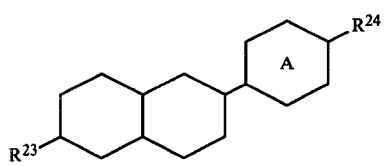   XXXVIII wherein ring A is aromatic or a trans-1,4-disubstituted cyclohexane ring; $R^{24}$ is methyl, —$CH_2R'$, —OR', —CO—R', —CN, —COOH, —CO—OR', —CO—SR' or —O—CO—R'; $R^{23}$ is hydrogen, methyl, —$CH_2R$, —OR or —$CH_2OR$, or when $R^{24}$ is methyl, —$CH_2R'$, —OR' or —CO—R', $R^{23}$ also can be —CN, —COOH, —CO—OR, —CO—SR or —O—CO—R; R and R' each are alkyl; and $R^{23}$ and $R^{24}$ each have up to 12 carbon atoms and together have at most 14 carbon atoms.

Compound XXI, XXIII, XXIV and XXXVIII are novel. Those compounds of formula XXI in which $R^{14}$ is cyano, straight-chain alkyl or straight-chain alkoxy and compounds of formula XXIII in which $R^{17}$ is cyano or straight-chain alkyl are suitable particularly as doping agents in liquid crystal mixtures and in general are not liquid crystalline themselves. With such doping agents, care must be taken that the mixtures also include at least one compound with liquid crystalline properties in a sufficient amount so that the total mixture has liquid crystalline properties. On the other hand, the remaining compounds of formulas XXI and XXIII as well as the compounds of formulas XXIV and XXXVIII are to a large extent themselves liquid crystalline.

In accordance with the invention, Compound XXI can be manufactured as follows:

(a) for Compound XXI in which $R^{14}$ is ester XXII, esterifying a compound of the formula

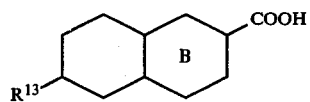   XXVI wherein $R^{13}$ and ring B are as above,
or a reactive derivative thereof (e.g., the corresponding acid chloride) with a compound of the formula

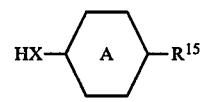   XXV wherein X, A and $R^{15}$ are as above;

(b) for Compound XXI in which $R^{14}$ is cyano, dehydrating a compound of the formula

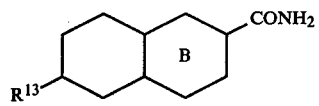   XXVII wherein $R^{13}$ and ring B are as above;

(c) for Compound XXI in which $R^{14}$ is straight-chain alkyl, reacting a compound of the formula

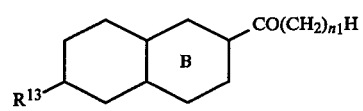   XXVIII wherein $n_1$ is an integer of 0 to 10 and $R^{13}$ and ring B are as above,
with hydrazine in the presence of a base;

(d) for Compound XXI in which ring B is saturated and $R^{14}$ is straight-chain alkoxy, etherifying a compound of the formula

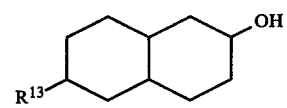   XXIX wherein $R^{13}$ is as above.

The compounds of formula XXV are known or can be made from known compounds by conventional techniques. The preparation of the compounds of formulas XXVI–XXIX is illustrated by the following Reaction Schemes A-C in which $R^{13}$, B and $n_1$ are as above, $n_2$ is of 1 to 10, the symbol (∼∼∼) indicates that the substituent in question can have the α- or β-configuration (below or above the plane of the formula) and the dotted line ( - - - ) indicates that one of the bonds denoted thereby is a double bond.
Scheme A
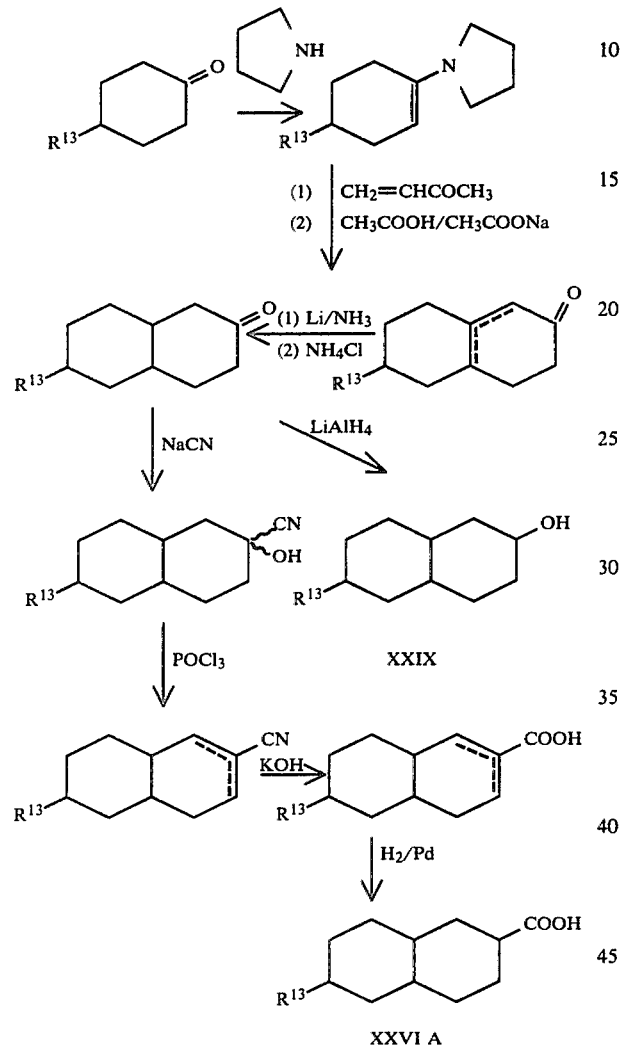
Scheme B
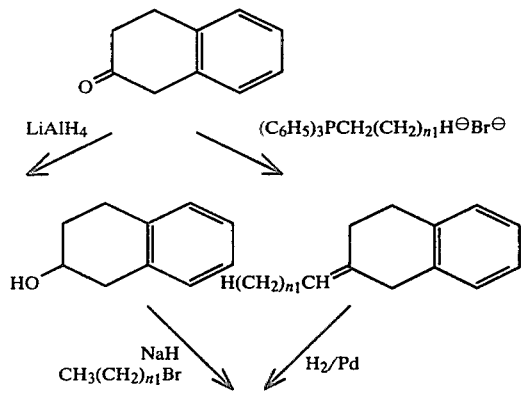
Scheme B
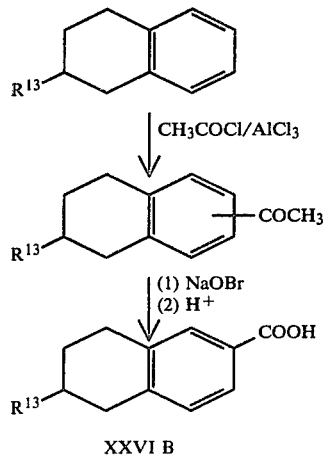
Scheme C
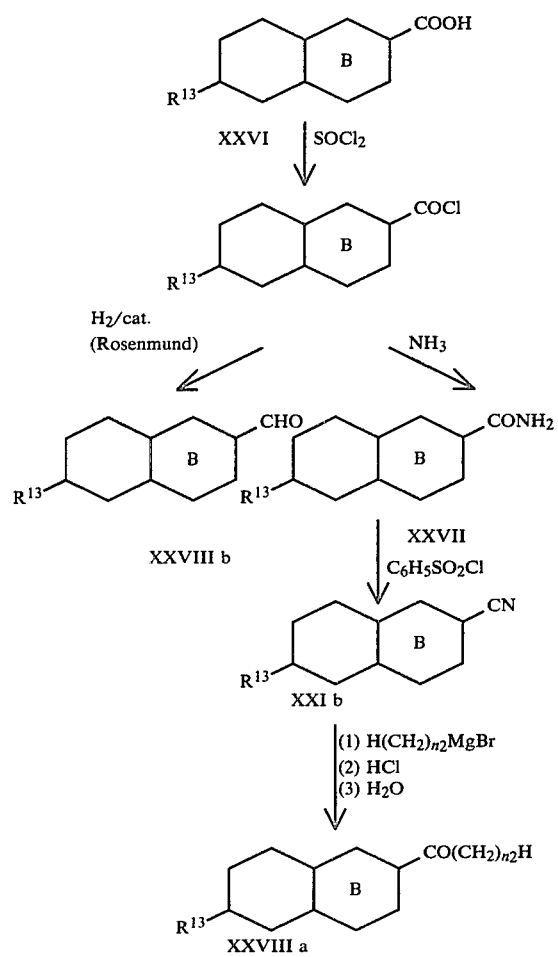
In accordance with the invention, the compounds of formula XXIII can be manufactured as follows:
(e) for Compound XXIII in which $R^{17}$ is ester XXII, esterifying a compound of the formula

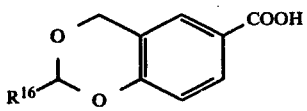

XXX wherein $R^{16}$ is as above,
with Compound XXV;

(f) for compound XXIII in which $R^{17}$ is cyano, dehydrating a compound of the formula

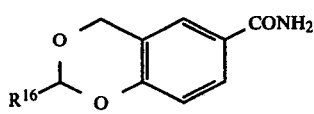

XXXI wherein $R^{16}$ is as above;

(g) for compound XXIII in which $R^{17}$ is straight-chain alkyl of 2 to 11 carbon atoms, catalytically hydrogenating a compound of the formula

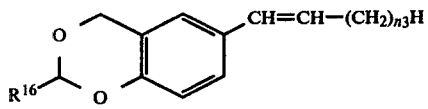

XXXII wherein $n_3$ is an integer of 0 to 9 and $R^{16}$ is as above;

(h) for Compound XXIII in which $R^{17}$ is methyl, reacting a compound of the formula

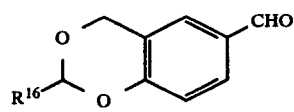

XXXIII wherein $R^{16}$ is as above,
with hydrazine in the presence of a base.

Starting materials XXX–XXXIII can be prepared according to the following Scheme D in which $R^{16}$ and $n_3$ are as above.

Scheme D

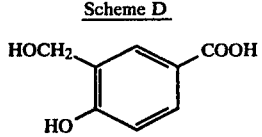

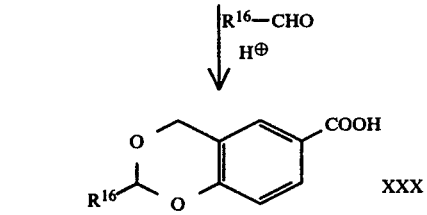

(1) ClCOOC₂H₅, N(C₂H₅)₃
(2) NH₃
LiAlH₄

-continued
Scheme D

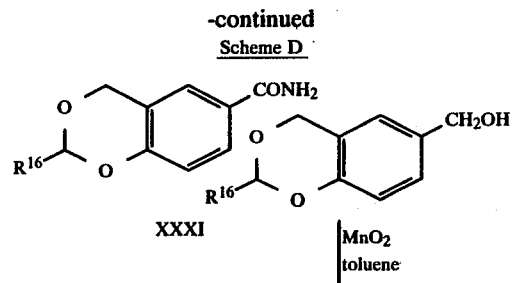

XXXI

MnO₂
toluene

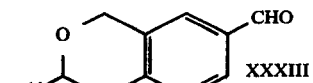

XXXIII $(C_6H_5)_3PCH_2(CH_2)_{n_3}H^{\ominus}Br^{\ominus}$

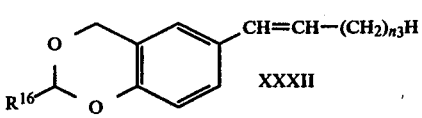

XXXII

In accordance with the invention, Compound XXIV can be manufactured as follows:

(i) for compound XXIV in which $R^{19}$ is alkyl, p-alkylphenyl or trans-4-alkylcyclohexyl, reacting a compound of the formula

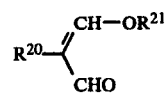

XXXIV with an acid addition salt (preferably the hydrochloride) of a compound of the formula

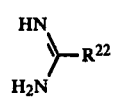

XXXV wherein one of $R^{20}$ and $R^{22}$ is trans-4-alkylcyclohexyl and the other is alkyl, p-alkylphenyl or trans-4-alkylcyclohexyl and $R^{21}$ is lower alkyl,
in the presence of a base (preferably an alcoholate);

(j) for Compound XXIV in which $R^{19}$ is cyano, dehydrating a compound of the formula

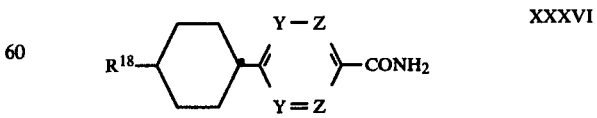

XXXVI wherein $R^{18}$, Y and Z are as above;

(k) for Compound XXIV in which Y is =CH—, Z is nitrogen and $R^{19}$ is cyano, dehydrating a compound of the formula

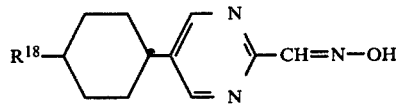
XXXVII wherein $R^{18}$ is as above.

Compound XXXIV and XXXV are known or can be prepared from known compounds by conventional techniques [Z. Naturforsch. 33 b, 433 (1978) and 34 b, 1535 (1979)].

The preparation of starting materials XXXVI and XXXVII is illustrated by the following Reaction Schemes E and F in which $R^{18}$ is as above.

Scheme E

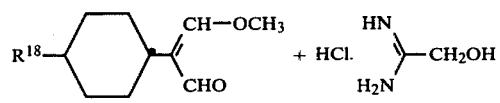
XXXIV a (1) NaOCH₃, CH₃OH
(2) H₃O⁺

-continued
Scheme E

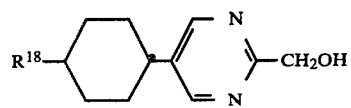

MnO₂, ClCH₂CH₂Cl (1) KMnO₄, K₂CO₃, H₂O
(2) H₃O⁺

NH₂OH·HCl pyridine (1) SOCl₂
(2) NH₃

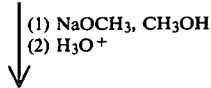
XXXVII

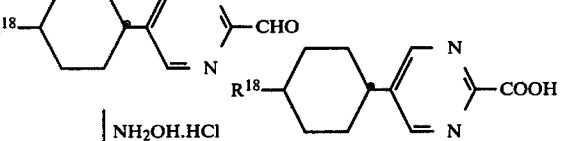
XXXVI a

Scheme F

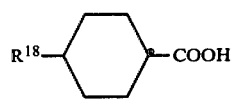

(1) SOCl₂
(2) NH₃

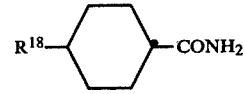
XXXVIII

C₆H₅SO₂Cl pyridine

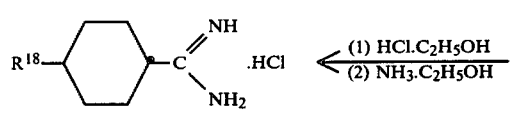

(1) HCl·C₂H₅OH
(2) NH₃·C₂H₅OH

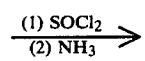
XXXIX

XXXV a (1) H₅C₂OCH=C(COOC₂H₅)
H₅C₂OOC
C₂H₅ONa, C₂H₅OH
(2) H₃O⁺

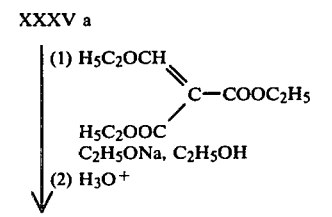

Scheme F

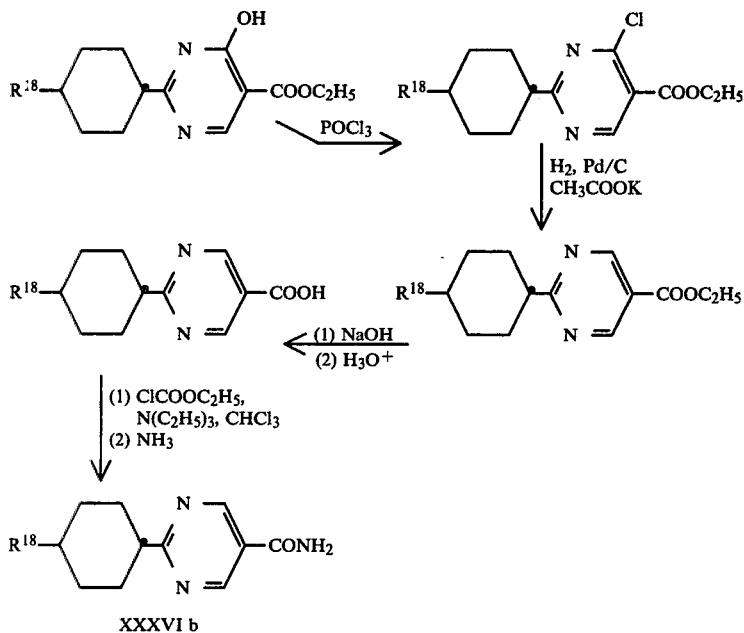

The starting materials used in Schemes E and F are known or can be prepared from known compounds by conventional techniques. Z. Naturforsch. 34 b, 1535 (1979) and in Mol. Cryst. Liq. Cryst. 37, 189 (1976) or 42, 215 (1977).

Compound XXXVIII can be manufactured on the basis of the following Reaction Schemes G-M. In these Schemes, A, R and R' are as above, R" is a readily cleavable alcohol protecting group; $R^{25}$ is hydrogen, methyl, $-CH_2R$, $-OR$, $-OR''$, $-CH_2OR$ or $-CH_2OR''$; $R^{26}$ is hydrogen or alkyl; $R^{27}$ is one of the values accorded to $R^{25}$ or $-CO-OR$ or $-O-CO-R$; $R^{28}$ is one of the values accorded to $R^{25}$ or $-CO-OR$, $-O-CO-R$ or $-COOH$; X is oxygen or sulphur; $X^1$ is bromine or iodine; Ts is p-tosyl; the symbol ∼∼∼ indicates that the bond in question can lie above or below the plane of the drawing (i.e. that the cyano group of Compound XXXIX can have the axial or equatorial configuration or the cyclohexane ring in Compound XLIII can be trans- or cis-disubstituted); in the remaining cases the representation of the (saturated) decalin structure means trans-decalin with equatorial configuration of the substituents.

Scheme G

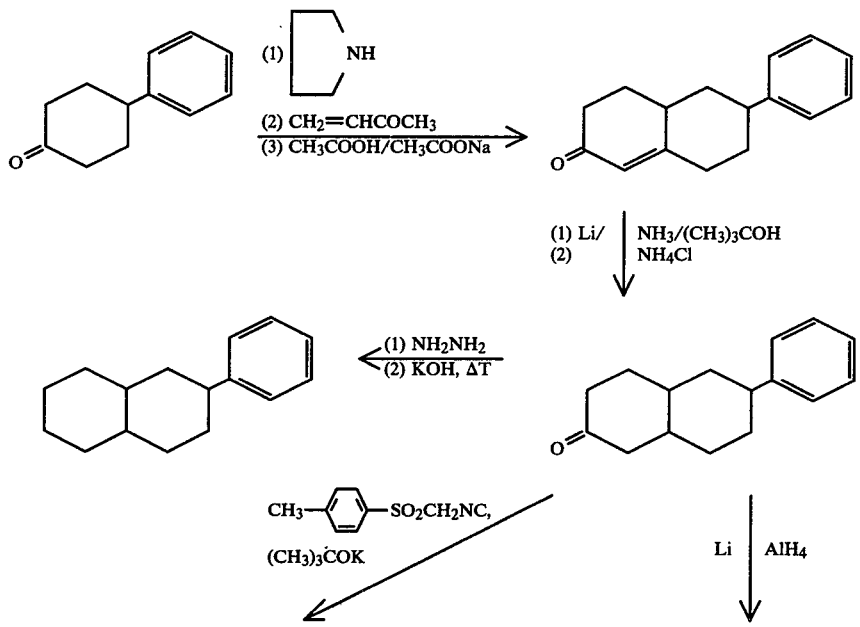

-continued
Scheme G
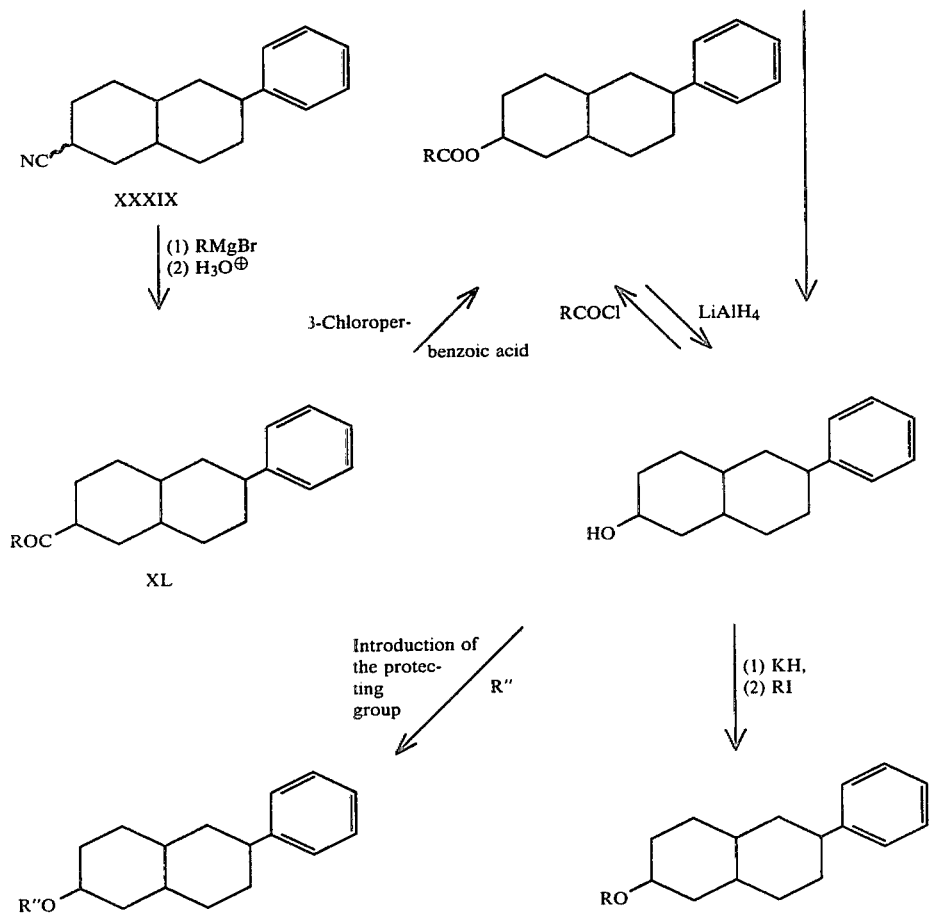
Scheme H
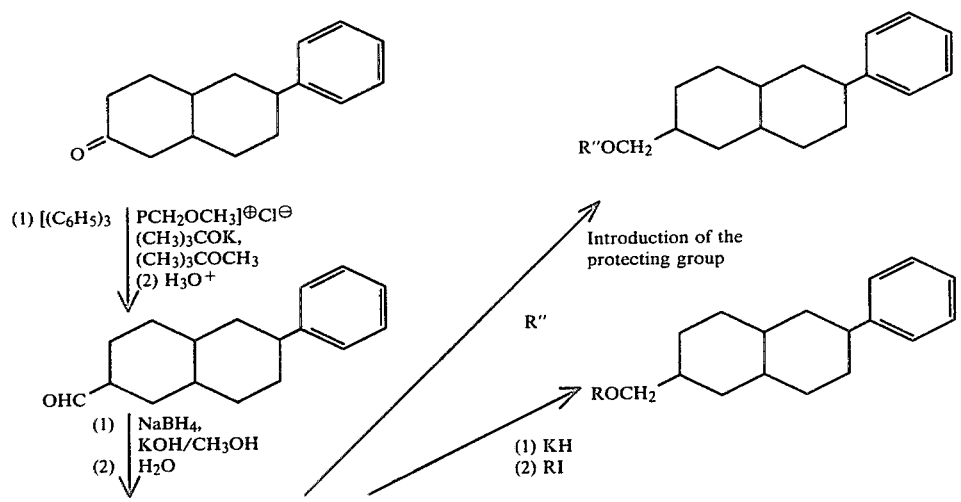

4,439,015
21                                    22
-continued
Scheme H
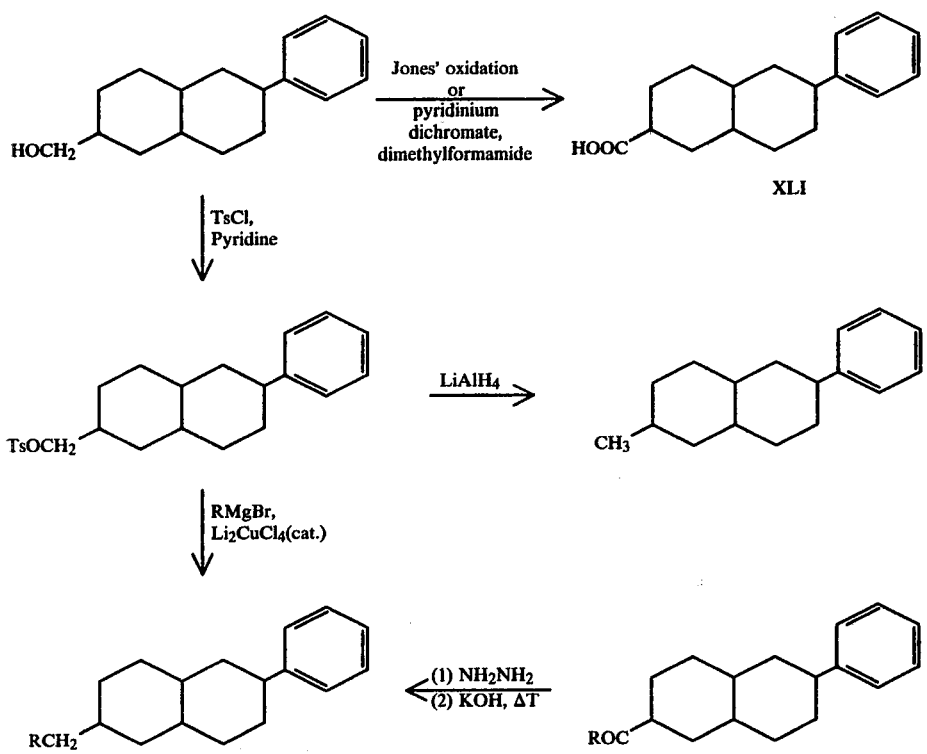
Scheme I
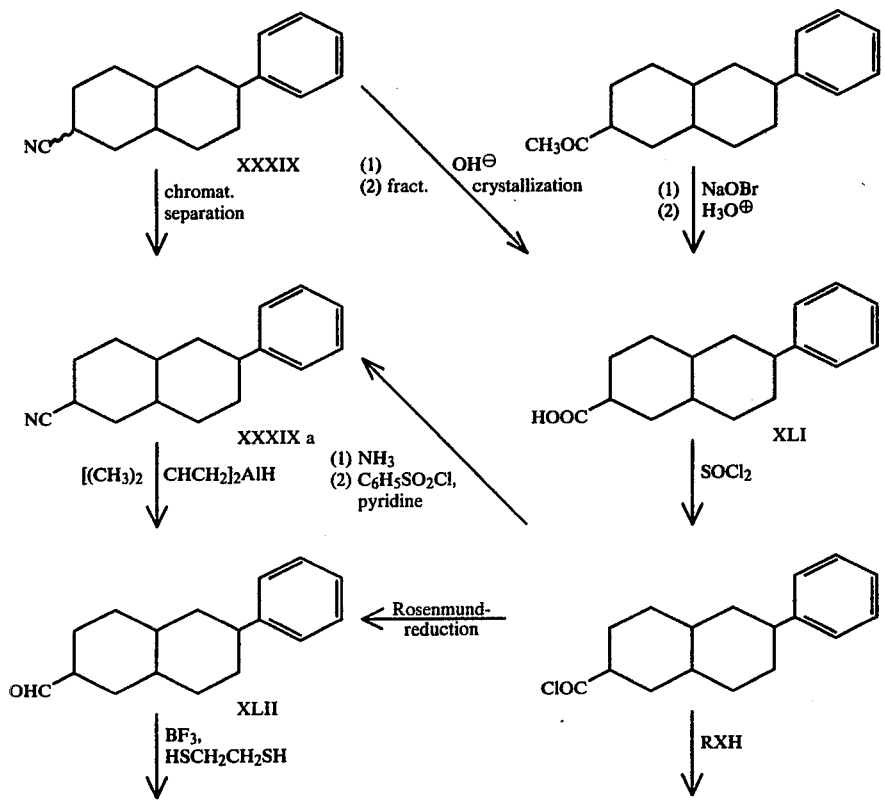

Scheme I
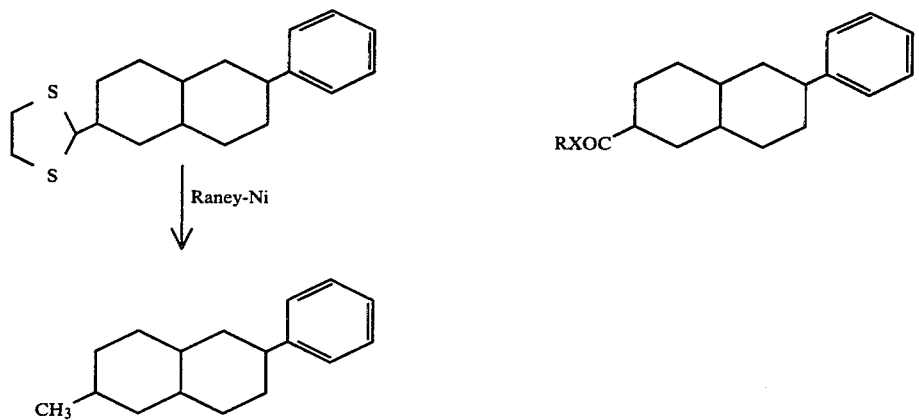
Scheme J
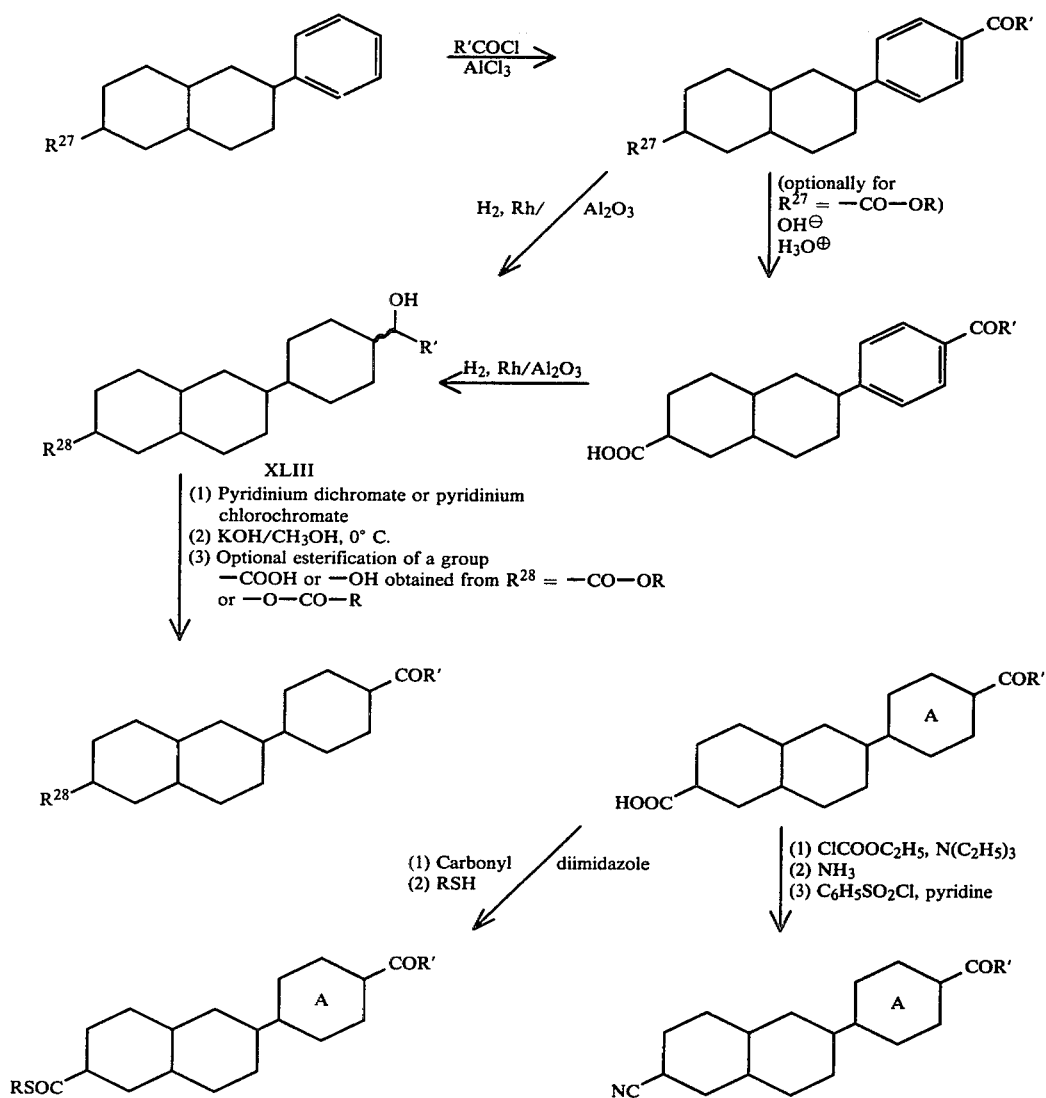

4,439,015
Scheme K
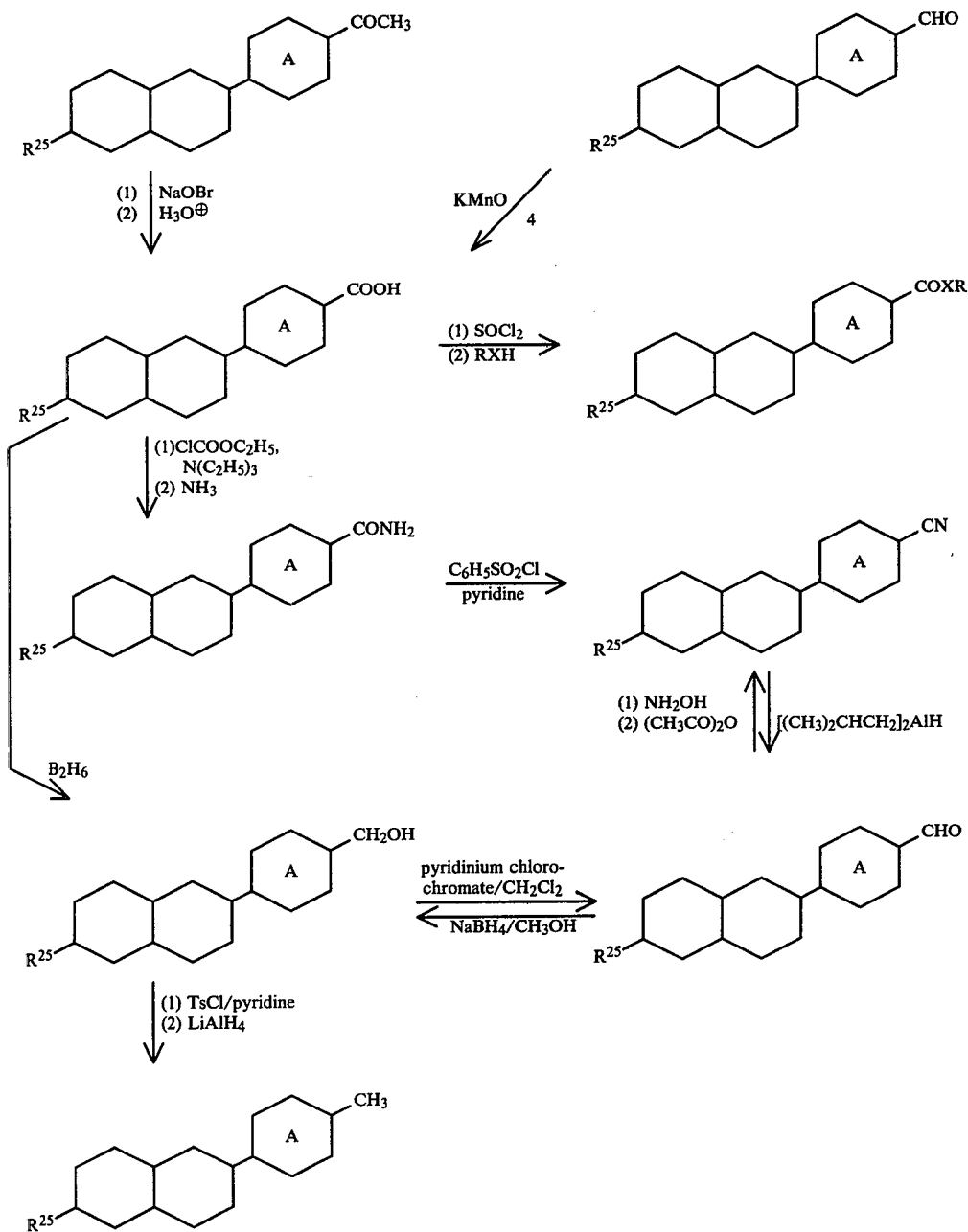
Scheme L
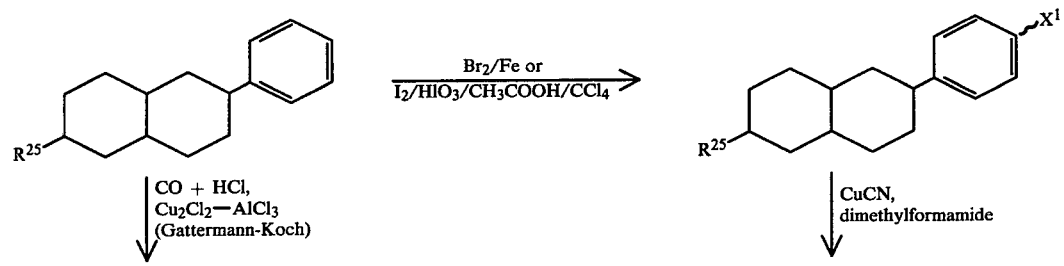

-continued
Scheme L
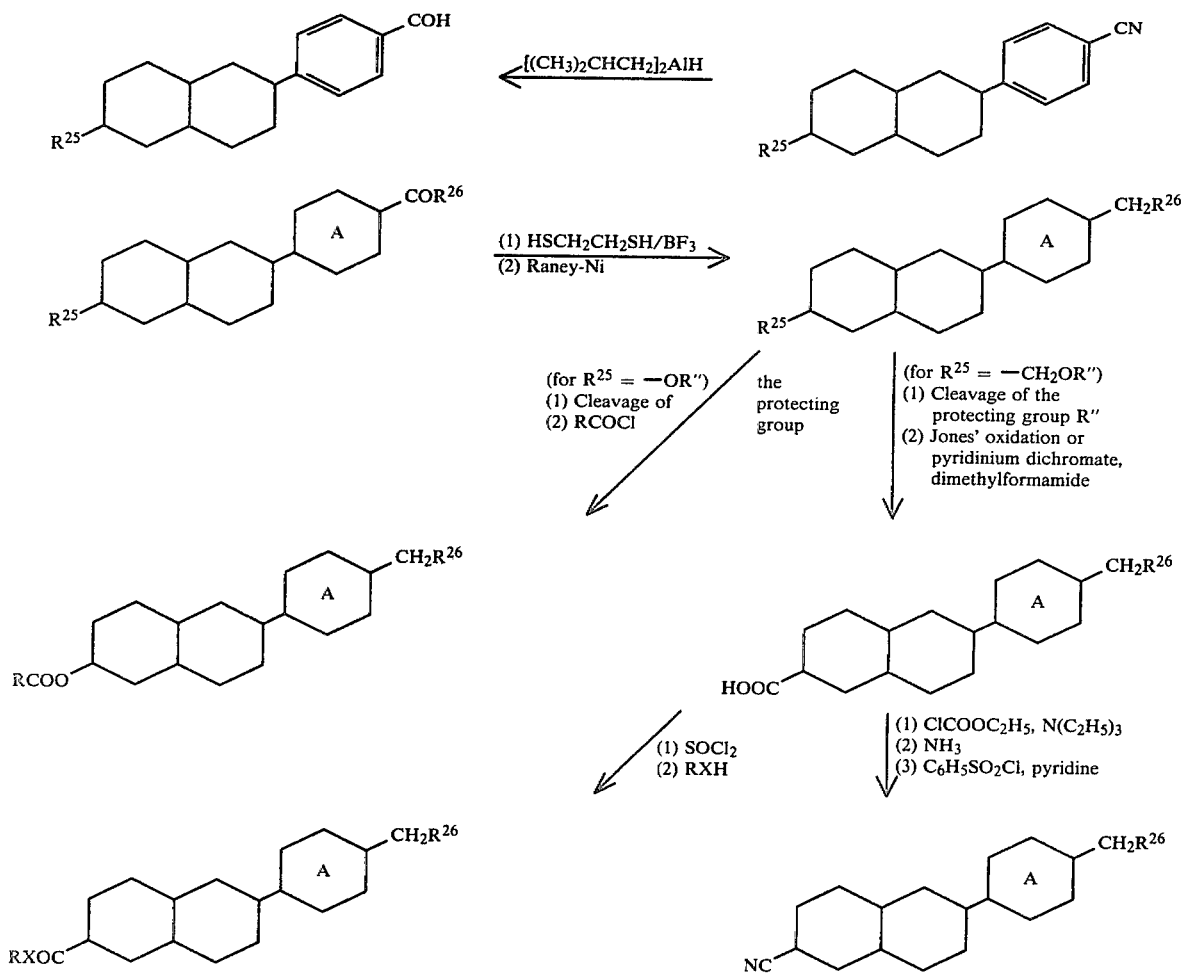
Scheme M
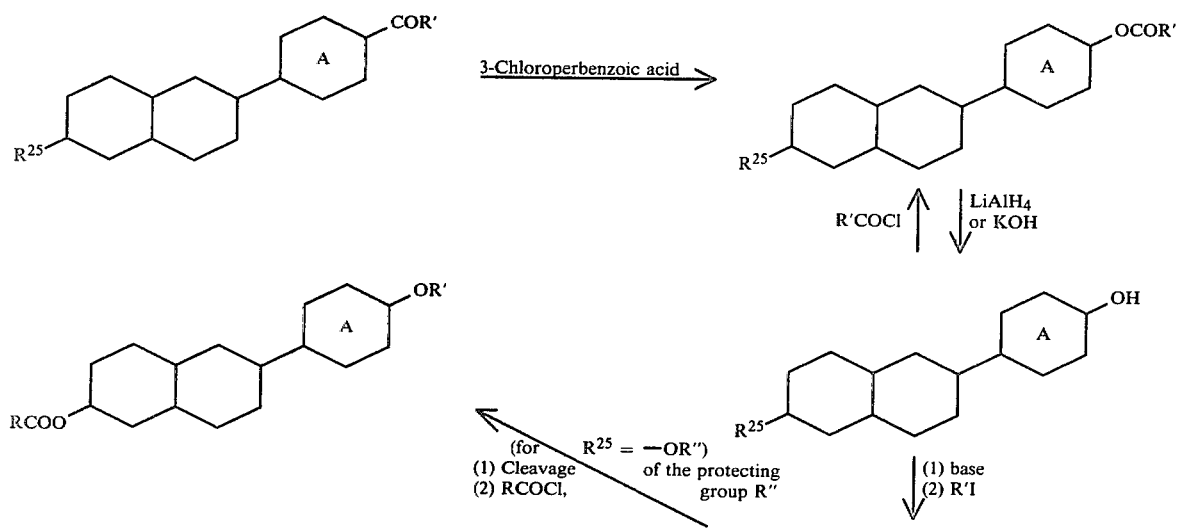

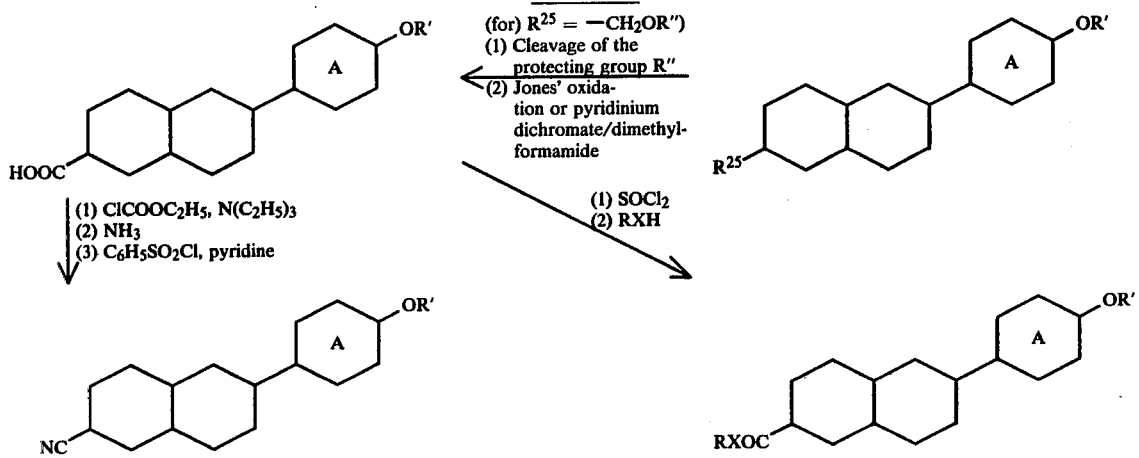

The diastereomeric mixture of Compound XXXIX can be separated by conventional chromatographic techniques. It, however, is preferred to convert the mixture into the acid XLI, separate by fractional crystallization and convert into the nitrile XXXIXa. On the other hand, if nitrile XXXIX is to be converted into Compound XL, then the separation is advantageously carried out only after the Grignard reaction and the subsequent equilibrating hydrolysis by crystallization of Compound XL.

Illustratively acid XLI can also be obtained from aldehyde XLII by oxidation with potassium permanganate.

If desired, the racemate of the acid of formula XLI can be resolved into the optical antipodes by conventional techniques. In so doing, acid XLI conveniently is reacted with an optically active base such as optically active phenylethylamine, ephedrine, cinchonidine, naphthylethylamine, methylbenzylamine and the like. The resulting mixture of diastereomeric salts is separated by crystallization and the resulting optically active salt is hydrolyzed. Thus, all compounds of formula XXXVIII can be obtained in optically active form starting from an optically active acid of formula XLI.

The term "readily cleavable alcohol dprotecting group" used for the R" embraces those alcohol protecting groups which can be cleaved off under conditions which do not affect an alkoxy group. Preferred examples of such —R" groups are benzyl and tetrahydropyranyl [Adv. Org. Chem. 3 (1963) 216], groups of the formulas —CH₂OCH₃ [J. Amer. Chem. Soc. 99, 1275 (1977)] and —CH₂OCH₂CH₂OCH₃ [Tetrahedron Letters 809 (1976)] t-butyl-dimethyl-silyl [J. Amer. Chem. Soc. 94, 6190 (1972)] and the like.

Illustratively, the benzyl group can be cleaved off by catalytic hydrogenation; palladium/carbon being the preferred catalyst. The group —CH₂OCH₃, the tetrahydropyranyl group and the t-butyl-dimethyl-silyl group can be removed by reaction with a strong acid such as sulphuric acid, hydrochloric acid, p-toluenesulphonic acid and the like. Illustratively, the removal of the group —CH₂OCH₂CH₂OCH₃ can be carried out by reaction with zine (II) bromide or titanium (IV) chloride in methylene chloride at room temperature. The t-butyl-dimethyl-silyl group can also be cleaved off by reaction with a fluoride, preferably an alkali metal fluoride or tetraalkylammonium fluoride such as potassium fluoride, tetrabutylammonium fluoride and the like. The introduction of such protecting groups can be carried out by reacting the alcohol to be protected with benzyl chloride, dihydropyran, chloromethyl methyl ether, β-methoxyethoxy-methyl chloride, t-butyl-dimethyl-silyl chloride and the like, if desired in the presence of a base. A detailed description relating to the introduction and cleavage of alcohol protecting groups is present in the literature mentioned earlier.

In addition to comprising one or more of Compound I, the inventive liquid crystal mixtures can include one or more of the following compounds:

4-Cyanobiphenyls of the formula

XXXXIV wherein $R^{29}$ is straight-chain alkyl or alkoxy of 2 to 7 carbon atoms;

trans-p-(4-alkylcyclohexyl)benzonitriles of the formula

VL wherein $R^{30}$ is straight-chain alkyl of 3 to 7 carbon atoms;

p-(5-alkyl-2-pyrimidinyl)benzonitriles of the formula

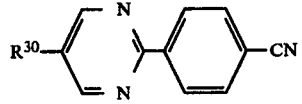

VLI wherein $R^{30}$ is as above, p-(trans-5-alkyl-m-dioxan-2-yl)benzonitriles of the formula

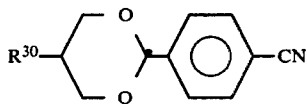

VLII wherein $R^{30}$ is as above;

p-alkylbenzoic acid p'-cyanophenyl esters of the formula

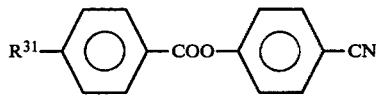

VLIII wherein $R^{31}$ is straight-chain alkyl of 2 to 7 carbon atoms;

trans-4-alkylcyclohexanecarboxylic acid phenyl esters of the formula

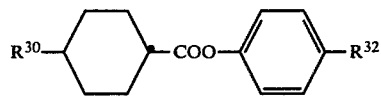

IL wherein $R^{30}$ is as above and $R^{32}$ is cyano or straight-chain alkoxy of 1 to 3 carbon atoms;

trans-p-[5-(4-alkylcyclohexyl)-2-pyrimidinyl]benzonitriles of the formula

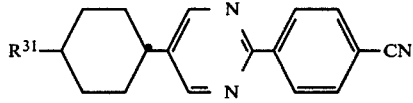

L wherein $R^{31}$ is as above; and/or 2-(trans-4-alkylcyclohexyl)-1-(p-cyanophenyl)-ethanes of the formula

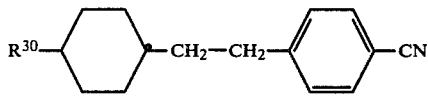

LI wherein $R^{30}$ is as above.

The weight ratio of the components of the inventive mixtures preferably corresponds to the eutectic composition. The amount of the compounds of formula I in the liquid crystal mixtures in accordance with the invention is, however, generally about 1 to about 90 mol percent, preferably about 10 to about 85 mol percent. The mixtures must, however, contain at least one liquid crystal compound in sufficient amount so that the total mixture also has liquid crystalline properties.

The inventive liquid crystalline mixtures can contain optically active compounds (illustratively, such compounds include optically active biphenyls) and/or dichroic coloring substances (e.g., azo, azoxy and anthraquinone coloring substances). The amount of such compounds in the mixtures is determined by the desired pitch, color, extinction, solubility and the like.

The inventive mixtures containing, inter alia, Compound I and other liquid crystalline and/or nonliquid crystalline compounds can be manufactured by conventional procedures. Illustratively, a mixture of the desired components can be heated to a temperature barely above the clearing point and subsequently cooled down.

In another aspect of the invention, Compound I (which is miscible with all known liquid crystals) can be used alone or in mixtures in all customary electro-optical devices. The choice of the components of the mixture generally depends on the purpose.

An electro-optical device containing one or more compounds of the formula I can be manufactured in a known manner. Illustratively, the device can be produced by evacuating a suitable cell and introducing the inventive compound or mixture into the evacuated cell.

The invention is also concerned with all novel compounds mixtures, processes, uses and devices as herein described.

The following nonlimiting Examples illustrate the invention. In particular, Examples 1–5 and 17 describe the manufacture of Compound I in accordance with the invention. Examples 5–6 illustrate preferred mixtures. Unless otherwise stated, percentages and ratios of solvent mixtures are given in volume and the temperatures are expressed in degrees Centigrade. Room temperature is 23° C. The ether is diethyl ether and the alcohol is ethanol. The symbol $\eta$ denotes viscosity (bulk viscosity ) and $\Delta\epsilon$ denotes the dielectric anisotropy. Compound XXI and XXXVIII each were used as the racemate of the two equatorial 2,6-disubstituted isomers. The abbreviations used for phase transitions have the following significances: C stands for crystalline, $S_A$ stands for smectic A, $S_B$ stands for smectic B, N stands for nematic and I stands for isotropic phase (e.g., $S_B$-N denotes a phase transition smectic B-nematic).

EXAMPLE 1

A mixture of 9.7 g of 4-ethoxy-α-trans-(4-pentyl-cyclohexyl)acetophenone, 125 ml of diethyleneglycol, 50 ml of ethanol, 6.2 g of hydrazine hydrate and 8.2 g of potassium hydroxide is heated to boiling for 4 hours at a bath temperature of 110° C. Thereafter, the bath temperature is increased to 220° C. and the ethanol and the excess hydrazine hydrate are allowed to distill off. Subsequently, the mixture is heated to an internal temperature of 180° C. for a further 4.5 hours, left to stand overnight, the mixture is poured into ice-water and the product is taken up in three 150 ml portions of ether. The combined organic phase is washed neutral with water, dried over sodium sulphate, evaporated and distilled in a bulb-tube at 180° C./about 1 Torr. The resulting 7.4 g of 2-(trans-4-pentylcyclohexyl)-1-(p-ethoxyphenyl)ethane (purity about 98.5%) are recrystallized once from isopropanol and once from diisopropyl ether at about—20° C.; m.p. (C-N) 18° C. or 27° C. (2 modifications), transition $S_B$-N 8° C. (monotropic), cl.p. (N-I) 47° C.

The 4-ethoxy-α-(trans-4-pentylcyclohexyl)acetophenone used as the starting material can be prepared as follows:

A mixture of 8.7 g of trans-4-pentylcyclohexylacetic acid chloride (prepared by boiling 8.0 g of trans-4-pentylcyclohexylacetic acid with 4.1 ml of thionyl chloride in 75 ml of benzene for 2 hours and subsequently evaporating the product) and 4.6 g of phenetole in 120 ml of dichloromethane is treated portionwise in an inert gas atmosphere with 5.5 g of aluminium chloride. The mixture is stirred at room temperature for 5 hours and then poured into ice-water which contains 50 ml of concentrated hydrochloric acid. The organic phase is separated and the aqueous phase is back-extracted with 300 ml of dichloromethane. The combined organic phase is washed in sequence with water, 3 N sodium hydroxide, water and saturated sodium chloride solution, dried over sodium sulphate, filtered and evaporated. There are obtained 9.7 g of crude, oily 4-ethoxy-α-(trans-4-pentylcyclohexyl)acetophenone.

The following compounds can be manufactured in an analogous manner:

2-(Trans-4-ethylcyclohexyl)-1-(p-ethoxyphenyl)ethane; m.p. (C-I) 20.5° C., cl.p. ($S_B$-I) 3° C. (monotropic);

2-(trans-4-ethylcyclohexyl)-1-(p-butyloxyphenyl)ethane; m.p. (C-N) 4° C., transition $S_B$-N 0° C. (monotropic), cl.p. (N-I) 6.5° C.;

2-(trans-4-ethylcyclohexyl)-1-(p-hexyloxyphenyl)ethane; m.p. (C-N) 10° C., transition $S_B$-N 1° C. (monotropic), cl.p. (N-I) 13° C.;

2-(trans-4-propylcyclohexyl)-1-(p-ethoxyphenyl)ethane; m.p. (C-N) 21° C., cl.p. (N-I) 34° C.;

2-(trans-4-propylcyclohexyl)-1-(p-propyloxyphenyl)ethane; m.p. (C-I) 20.5° C., transition $S_B$-N 13.5 ° C. (monotropic), cl.p. (N-I) 19.5° C. (monotropic);

2-(trans-4-propylcyclohexyl)-1-(p-butyloxyphenyl)ethane; m.p. (C-N) 20.5° C., transition $S_B$-N 20° C. (monotropic), cl.p. (N-I) 33° C.;

2-(trans-4-butylcyclohexyl)-1-(p-methoxyphenyl)ethane; m.p. (C-I) 28° C., cl.p. (N-I) 16.5° C. (monotropic);

2-(trans-4-butylcyclohexyl)-1-(p-ethoxyphenyl)ethane; m.p. (C-$S_B$) 10° C., transition $S_B$-N 11° C., cl.p. (N-I) 32° C.;

2-(trans-4-butylcyclohexyl)-1-(p-butyloxyphenyl)ethane; m.p. (C-$S_B$) 11° C., cl.p. ($S_B$-I) 37° C.;

2-(trans-4-pentylcyclohexyl)-1-(p-methoxyphenyl)ethane; m.p. (C-N) 31° C., cl.p. (N-I) 33° C.;

2-(trans-4-pentylcyclohexyl)-1-(p-propyloxyphenyl)ethane; m.p. (C-$S_B$) 24.5° C., transition $S_B$-N 32.5° C., cl.p. (N-I) 33.5° C.;

2-(trans-4-pentylcyclohexyl)-1-(p-butyloxyphenyl)ethane; m.p. (C-$S_B$) 25.5° C., transition $S_B$-N 44° C., cl.p. (N-I) 45° C.;

2-(trans-4-heptylcyclohexyl)-1-(p-methoxyphenyl)ethane; m.p. (C-N) 28.5° C., transition $S_B$-N 17° C. (monotropic), cl.p. (N-I) 40° C.;

2-(trans-4-heptylcyclohexyl)-1-(p-ethoxyphenyl)ethane; m.p. (C-N) 36° C., transition $S_B$-N 30° C. (monotropic), cl.p. (N-I) 51° C.;

2-(trans-4-propylcyclohexyl)-1-(p-pentylphenyl)ethane; m.p. (C-$S_B$) 3° C., cl.p. ($S_B$-I) 6° C.;

2-(trans-4-pentylcyclohexyl)-1-(p-propylphenyl)ethane; m.p. (C-$S_B$) 4.5° C., cl.p. ($S_B$-I) 18° C.;

2-(trans-4-pentylcyclohexyl)-1-(p-pentylphenyl)ethane; m.p. (C-$S_B$) 9.5° C., cl.p. ($S_B$-I) 30° C.;

2-(trans-4-pentylcyclohexyl)-1-(p-hexylphenyl)ethane; m.p. (C-$S_B$) 11° C., cl.p. ($S_B$-I) 34° C.;

2-(trans-4-heptylcyclohexyl)-1-(p-butylphenyl)ethane; m.p. (C-$S_B$) 3.5° C., cl.p. ($S_B$-I) 30.5° C.; crystallization from the $S_B$-phase could not be achieved even upon cooling to −24° C.

EXAMPLE 2

A mixture of 4.3 g of 4-(4′-pentylphenyl)-α-(trans-4-propylcyclohexyl)acetophenone, 75 ml of diethyleneglycol, 25 ml of ethanol, 2.2 g of hydrazine hydrate and 7.0 g of potassium hydroxide is heated to boiling for 4 hours at a bath temperature of 110° C. Thereafter, the bath temperature is increased to 220° C. and the ethanol and the excess hydrazine hydrate are allowed to distil off. Subsequently, the mixture is heated to an innternal temperature of 180° C. for a further 5 hours, left to cool, diluted with water and extracted with diethyl ether. The organic phase is washed neutral with water, dried over sodium sulphate and evaporated. The yellow foam obtained (3.9 g) is "recrystallized" once from isopropanol and once from ethanol. There are obtained 2.7 g of 2-(trans-4-propylcyclohexyl)-1-(4′-pentyl-4-biphenylyl)ethane which is presumably smectic at room temperature; phase transitions at 43.5° C. and 130° C., transition $S_A$-N 132.5° C., cl.p. (N-I) 141.5° C.

The 4-(4′-pentylphenyl)-α-(trans-4-propylcyclohexyl)acetophenone used as the starting material can be prepared as follows:

A mixture of 3.5 g of trans-4-propylcyclohexylacetic acid chloride and 4.0 g of 4-pentylbiphenyl in 125 ml of dichloromethane is treated portionwise within 15 minutes with 2.6 g of aluminium chloride. The mixture is stirred at room temperature for 5 hours and then poured into 250 ml of 2 N hydrochloric acid. The organic phase is separated and the aqueous phase is back-extracted with two 150 ml portions of dichloromethane. The combined organic phase is washed in sequence with water, 1 N sodium hydroxide and water, dried over sodium sulphate and evaporated. The crude product is dissolved in boiling acetone and filtered while hot with a small amqunt of active carbon. 4-(4′-Pentylphenyl)-α-(trans-4-propylcyclohexyl)acetophenone crystallizes out upon cooling. Yield 4.3 g; m.p. (C-$S_A$) 100° C., cl.p. ($S_A$-I) 143° C.

The following compounds can be manufactured in an analogous manner:

2-(Trans-4-ethylcyclohexyl)-1-(4′-propyl-4-biphenylyl)ethane; m.p. about 55° C., transition S-$S_B$ 51.5° C., transition $S_B$-N 98.5° C., cl.p. (N-I) 121.5° C.;

2-(trans-4propylcyclohexyl)-1-(4′-butyloxy-4-biphenylyl)ethane; m.p. (C-S) 84.5° C., transition S-$S_A$ 139.5° C., transition $S_A$-N 152.5° C., cl.p. (N-I) 172.5° C.

EXAMPLE 3

(a) In an analogous manner to Example 1 there is manufactured p-[2-(trans-4-butylcyclohexyl)ethyl]phenol (solvent in the Friedel-Crafts acylation of the phenol: nitrobenzene or nitromethane); m.p. 101.5°–102.5° C.

(b) A solution of 0.68 g of butyric acid chloride in 3 ml of benzene is added dropwise while stirring to a solution of 1.6 g of p-[2-(trans-4-butylcyclohexyl)ethyl]phenol in 5 ml of dry pyridine. The mixture is left to stand overnight, then poured into ice/water and extracted with diethyl ether. The organic phase is washed several times with 3 N hydrochloric acid, washed neutral with water, dried over sodium sulphate and evaporated. The smectic crude product (2.05 g) is purified by chromatography on silica gel with hexane/diethyl ether (19:1). The fractions which are pure according to thin-layer chromatography (1.9 g) are recrystallized once from isopropanol and once from ethanol at −20° C. There is obtained 0.8 g of analytically pure p-[2-(trans-4-butylcyclohexyl)-1-ethyl]phenylbutyrate; m.p. −13° C. or +4° C. (2 modifications), cl.p. ($S_B$-I) 45° C.

p-[2-(Trans-4-butylcyclohexyl)ethyl]phenol can also be obtained in the following manner:

A solution of 4.7 g of 2-(trans-4-butylcyclohexyl)-1-(p-methoxyphenyl)ethane (manufactured according to Example 1) in 50 ml of dichloromethane is added dropwise to a solution of 6.9 g of aluminium chloride in 100 ml of dichloromethane and 10 ml of ethyl mercaptan, the mixture is stirred at room temperature for 4 hours, then poured into ice/water, the organic phase is separated and the aqueous phase is extracted twice with 100 ml of dichloromethane each time. The combined organic phase is washed neutral with saturated sodium chloride solution, dried over sodium sulphate and evaporated. The resulting crude p-[2-(trans-4-butylcyclohexyl)ethyl]phenol (4.4 g) is recrystallized from hexane. Yield 3.8 g; m.p. 101.5°–102.5° C.

The following compounds can be manufactured in an analogous manner:

p-[2-(Trans-4-butylcyclohexyl)-1-ethyl]phenylacetate:
  m.p. (C-I) 32.5° C., cl.p. (N-I) 23° C. (monotropic);
p-[2-(trans-4-pentylcyclohexyl)-1-ethyl]phenylacetate;
  m.p. (C-I) 41.5° C., cl.p. (N-I) 40.5° C. (monotropic);
p-[2-(trans-4-pentylcyclohexyl)-1-ethyl]phenylbutyrate;
  m.p. (C-S$_B$) 31° C., cl.p. (S$_B$-I) 52° C.

EXAMPLE 4

A mixture of 4.6 g of 2-(trans-4-propylcyclohexyl)-1-phenylethane (manufactured analogously to Example 1 by Friedel-Crafts acylation of benzene and reduction of the ketone obtained) and 1.94 g of propionic acid chloride in 100 ml of dichloromethane is treated portionwise under an inert gas atmosphere with 3.2 g of aluminium chloride. The mixture is stirred at room temperature for 5 hours and poured into ice/water with which are admixed 25 ml of concentrated hydrochloric acid. The organic phase is separated and the aqueous phase is back-extracted twice with 100 ml of dichloromethane each time. The combined organic phase is washed with 1 N sodium hydroxide, washed neutral with water, dried over sodium sulphate and evaporated. The resulting p-[2-(trans-4-propylcyclohexyl)-1-ethyl]propiophenone (5.5 g) is recrystallized twice from ethanol; m.p. (C-N) 40° C., cl.p. (N-I) 56° C.

The following compounds can be manufactured in an analogous manner:

p-[2-(Trans-4-propylcyclohexyl)-1-ethyl]valerophenone; m.p. (C-I) 47.5° C., transition S$_B$-N 30° C. (monotropic), cl.p. (N-I) 46° C. (monotropic);
p-[2-(trans-4-pentylcyclohexyl)-1-ethyl]valerophenone;
  m.p. (C-N) 48.5° C., transition S$_B$-S$_A$ 33° C. (monotropic), transition S$_A$-N 39° C. (monotropic), cl.p. (N-I) 57° C.

EXAMPLE 5

5 mol % of p-(5-pentyl-2-pyrimidinyl)benzonitrile,
9 mol % of p-(5-heptyl-2-pyrimidinyl)benzonitrile,
16 mol % of trans-4-pentylcyclohexanecarboxylic acid p-methoxyphenyl ester,
25 mol % of trans-4-pentylcyclohexanecarboxylic acid p-propyloxyphenyl ester,
6 mol % of p-[5-(trans-4-pentylcyclohexyl)-2-pyrimidinyl]benzonitrile,
8 mol % of p-[(4aαH,8aβH)-decahydro-6β-propyl-2α-napththyl]benzonitrile,
6 mol % of p-[(4aαH,8aβH-decahydro-6β-pentyl-2α-naphthyl]benzonitrile,
25 mol % of 2-[trans-4-pentylcyclohexyl)-1-(p-ethoxyphenyl)ethane;
  m.p. <0° C., cl.p. 69° C., η (22° C.)=28.2 cp, nematic.

EXAMPLE 6

6 mol % of p-(5-pentyl-2-pyrimidinyl)benzonitrile,
12 mol % of p-(5-heptyl-2-pyrimidinyl)benzonitrile,
20 mol % of trans-4-pentylcyclohexanecarboxylic acid p-methoxyphenyl ester,
26 mol % of trans-4-pentylcyclohexanecarboxylic acid p-propyloxyphenyl ester,
8 mol % of p-[(4aαH,8aβH)-decahydro-6β-ethyl-2α-naphthyl]benzonitrile,
8 mol % of p-[(4aαH,8aβH)-decahydro-6β-propyl-2α-naphthyl]benzonitrile,
8 mol % of p-[(4aαH,8aβH)-decahydro-6β-pentyl-2α-naphthyl]benzonitrile,
12 mol % of 2-(trans-4-heptylcyclohexyl)-1-(p-ethoxyphenyl)ethane;
  m.p. <0° C., cl.p. 63.5° C., η (22° C.)=32.5 cp, nematic.

EXAMPLE 7

7 mol % of p-(5-pentyl-2-pyrimidinyl)benzonitrile,
13 mol % of p-(5-heptyl-2-pyrimidinyl)benzonitrile,
21 mol % of trans-4-pentylcyclohexanecarboxylic acid p-methoxyphenyl ester,
27 mol % of trans-4-pentylcyclohexanecarboxylic acid p-propyloxyphenyl ester,
11 mol % of p-[5-(trans-4-ethylcyclohexyl)-2-pyrimidinyl]benzonitrile,
8 mol % of p-[5-(trans-4-pentylcyclohexyl)-2-pyrimidinyl]benzonitrile,
13 mol % of 2-(trans-4-heptylcyclohexyl)-1-(p-ethoxyphenyl)ethane;
  m.p. <0° C., cl. p. 80° C., nematic.

EXAMPLE 8

5 mol % of p-(5-pentyl-2-pyrimidinyl)benzonitrile,
8 mol % of p-(5-heptyl-2-pyrimidinyl)benzonitrile,
14 mol % of trans-4-pentylcyclohexanecarboxylic acid p-methoxyphenyl ester,
21 mol % of trans-4-pentylcyclohexanecarboxylic acid p-propyloxyphenyl ester,
9 mol % of p-[5-(trans-4-ethylcyclohexyl)-2-pyrimidinyl]benzonitrile,
6 mol % of p-[5-(trans-4-pentylcyclohexyl)-2-pyrimidinyl]benzonitrile,
37 mol % of 2-(trans-4-pentylcyclohexyl)-1-(p-ethoxyphenyl)ethane;
  m.p. <0° C., cl.p. 70° C., η (22° C.)=26.3 cp, nematic.

EXAMPLE 9

17 mol % of trans-4-butylcyclohexanecarboxylic acid p-ethoxyphenyl ester,
19 mol % of trans-4-butylcyclohexanecarboxylic acid p-pentyloxyphenyl ester,
16 mol % of trans-4-pentylcyclohexanecarboxylic acid p-methoxyphenyl ester,
22 mol % of trans-4-pentylcyclohexanecarboxylic acid p-propyloxyphenyl ester,
26 mol % of 2-(trans-4-pentylcyclohexyl)-1-(p-ethoxyphenyl)ethane;
  m.p. <0° C., cl.p. 62.2° C., η (22° C.)=21.0 cp, Δε= −1.09, nematic.

EXAMPLE 10

6 mol % of p-(5-pentyl-2-pyrimidinyl)benzonitrile,
12 mol % of p-(5-heptyl-2-pyrimidinyl)benzonitrile,
19 mol % of trans-4-pentylcyclohexanecarboxylic acid p-methoxyphenyl ester,
12 mol % of p-[5-(trans-4-ethylcyclohexyl)-2-pyrimidinyl]benzonitrile, 7 mol % of p-[5-(trans-4-pentylcyclohexyl)-2-pyrimidinyl]benzonitrile,
12 mol % of p-[2-(trans-4-heptylcyclohexyl)ethyl]benzonitrile,
32 mol % of 2-(trans-4-propylcyclohexyl)-1-(p-butyloxyphenyl)ethane;
m.p. <0° C., cl.p. 69° C., η (22° C.)=28.5 cp, nematic.

EXAMPLE 11

5 mol % of p-(5-pentyl-2-pyrimidinyl)benzonitrile,
9 mol % of p-(5-heptyl-2-pyrimidinyl)benzonitrile,
16 mol % of trans-4-butylcyclohexanecarboxylic acid p-ethoxyphenyl ester,
15 mol % of trans-4-pentylcyclohexanecarboxylic acid p-methoxyphenyl ester,
11 mol % of p-[5-(trans-4-ethylcyclohexyl)-2-pyrimidinyl]benzonitrile,
7 mol % of p-[5-(trans-4-pentylcyclohexyl)-2-pyrimidinyl]benzonitrile,
37 mol % of 2-(trans-4-propylcyclohexyl)-1-(p-ethoxyphenyl)ethane;
m.p. <0° C., cl.p. 71° C., η (22° C.)=28.2 cp, nematic.

EXAMPLE 12

5 mol % of p-butylbenzoic acid p'-cyanophenyl ester,
5 mol % of p-(5-pentyl-2-pyrimidinyl)benzonitrile,
9 mol % of p-(5-heptyl-2-pyrimidinyl)benzonitrile,
10 mol % of p-[5-(trans-4-ethylcyclohexyl)-2-pyrimidinyl]benzonitrile,
34 mol % of p-[2-trans-4-pentylcyclohexyl)ethyl]benzonitrile,
37 mol % of 2-(trans-4-propylcyclohexyl)-1-(p-ethoxyphenyl)ethane;
m.p. <−10° C., cl.p. 54° C., η (22° C.)=27.0 cp, nematic.

EXAMPLE 13

4 mol % of p-(5-pentyl-2-pyrimidinyl)benzonitrile,
7 mol % of p-(5-heptyl-2-pyrimidinyl)benzonitrile,
12 mol % of trans-4-butylcyclohexanecarboxylic acid p-ethoxyphenyl ester,
11 mol % of trans-4-pentylcyclohexanecarboxylic acid p-methoxyphenyl ester,
9 mol % of p-[5-(trans-4-ethylcyclohexyl)-2-pyrimidinyl]benzonitrile,
5 mol % of 6-pentyl-trans-decalin-2-carboxylic acid p-ethylphenyl ester,
7 mol % of 6-butyl-trans-decalin-2-carboxylic acid trans-4-pentyl-1-cyclohexyl ester,
27 mol % of p-[2-(trans-4-pentylcyclohexyl)ethyl]benzonitrile,
18 mol % of 2-(trans-4-propylcyclohexyl)-1-(p-butyloxyphenyl)ethane;
m.p. <−10° C., cl.p. 63° C., η (22° C.)=27.0 cp, nematic.

EXAMPLE 14

3 mol % of p-(5-pentyl-2-pyrimidinyl)benzonitrile,
8 mol % of p-(5-heptyl-2-pyrimidinyl)benzonitrile,
10 mol % of trans-4-butylcyclohexanecarboxylic acid p-ethoxyphenyl ester,
9 mol % of trans-4-pentylcyclohexanecarboxylic acid p-methoxyphenyl ester,
15 mol % of trans-4-pentylcyclohexanecarboxylic acid p-propyloxyphenyl ester
7 mol % of p-[5-(trans-4-ethylcyclohexyl)-2-pyrimidinyl]benzonitrile,
9 mol % of p-[5-(trans-4-heptylcyclohexyl)-2-pyrimidinyl]benzonitrile,
24 mol % of 2-(trans-4-propylcyclohexyl)-1-(p-ethoxyphenyl)ethane;
15 mol % of 2-(trans-4-propylcyclohexyl)-1-(p-butyloxyphenyl)ethane;
m.p. <−10° C., cl.p. 69° C., η (22° C.)=25.8 cp, nematic.

EXAMPLE 15

4 mol % of p-(5-pentyl-2-pyrimidinyl)benzonitrile,
6 mol % of p-(5-heptyl-2-pyrimidinyl)benzonitrile,
13 mol % of trans-4-butylcyclohexanecarboxylic acid p-ethoxyphenyl ester,
12 mol % of trans-4-pentylcyclohexanecarboxylic acid p-methoxyphenyl ester,
8 mol % of p-[5-(trans-4-ethylcyclohexyl)-2-pyrimidinyl]benzonitrile,
10 mol % of p-[5-(trans-4-heptylcyclohexyl)-2-pyrimidinyl]benzonitrile,
29 mol % of p-[2-(trans-4-pentylcyclohexyl)ethyl]-benzonitrile,
18 mol % of 2-(trans-4-propylcyclohexyl)-1-(p-butyloxyphenyl)-ethane;
m.p. <−10° C., cl.p. 74° C., η (22° C.)=28.3 cp, nematic.

EXAMPLE 16

8 mol % of p-(5-pentyl-2-pyrimidinyl)benzonitrile,
14 mol % of p-(5-heptyl-2-pyrimidinyl)benzonitrile,
23 mol % of trans-4-pentylcyclohexanecarboxylic acid p-methoxyphenyl ester,
29 mol % of trans-4-pentylcyclohexanecarboxylic acid p-propyloxyphenyl ester,
11 mol % of trans-4-(p-pentylphenyl)cyclohexanecarboxylic acid trans-4-propylcyclohexyl ester,
15 mol % of 2-(trans-4-heptylcyclohexyl)-1-(p-ethoxyphenyl)ethane;
m.p. <0° C., cl.p. 60.3° C., η (22° C.)=30.0 cp, nematic.

EXAMPLE 17

(a) A mixture of 182.3 g of trans-4-pentylcyclohexanecarboxaldehyd, 2 l of methylene chloride and 589.6 g of (p-methoxycarbonylphenyl)methyl-triphenylphosphonium bromide is cooled to 0°–5° C. and, thereafter, the cold solution is treated at 0°–5° C. within ca. 1 hour with a solution of 27.6 g sodium in 276 ml of methanol (1.2 moles of sodium methylate). The obtained brown-red solution is stirred at 0°–5° C. for a further 15 minutes and, then, the temperature is left to rise to room temperature. The solution is stirred at room temperature for 1 hour, then poured into a stirring vessel and washed with 1 liter of 5% sodium bicarbonate solution. The upper colorless phase is back-extracted with 250 ml of methylene chloride. The combined methylene chloride phases are dried over sodium sulphate, filtered and partly evaporated, while a total amount of 5 l of methanol is added continuously through a dropping funnel. When a reaction volume of 4 l and a distillation temperature of 63° C. is reached, the reaction mixture is cooled to −20° C. and treated at this temperature with 400 ml of water within 30 minutes while stirring. The p-[2-(trans-4-pentylcyclohexyl)ethenyl]benzoic acid methyl ester, which crystallizes, is suction filtered, washed with 1 liter of 90% methanol at −20° C. and the solvent is pressed well from the crystalline mass.

(b) The obtained crystalline mass is dissolved in 1.5 l of methylene chloride and washed with 750 ml of water. The aqueous phase is back-extracted with 250 ml methylene chloride and then the combined methylene chloride phases are dried over sodium sulphate, filtered and concentrated to a volume of 1.5 l. 5 ml of triethylamine and 5 g of palladium/carbon (5%) are added and the mixture is hydrogenated after gassing the hydrogenation flask twice with hydrogen, while shaking at room temperature. After 2 hours the hydrogen uptake comes to a standstill and the catalyst is filtered off and washed with 250 ml of methylene chloride. The filtrate is treated with 30 g of activated carbon, stirred and filtered. The filter residue is back-washed with 250 ml of methylene chloride and the filtrate is evaporated on a rotary evaporator. The colorless oily residue is treated with 1 liter of methanol and heated at reflux on a steam bath while stirring, whereby the oil is dissolved almost completely. The mixture is cooled while stirring and the product left to crystallize at −25° C. The crystalline product is filtered off and washed with 250 ml of methanol at −25° C. and the solvent is pressed well from the crystalline mass. After drying at room temperature in a stream of nitrogen under reduced pressure, there are obtained 252 g of crystalline p-[2-(trans-4-pentylcyclohexyl)-1-ethyl]benzoic acid methyl ester, which can be further purified by chromatography on silica gel with toluene and recrystallization from pentane; m.p. (C-N) 36.7° C., cl.p. (N-I) 48.7° C.

The following compounds can be manufactured in an analogous manner:

p-[2-(trans-4-ethylcyclohexyl)-1-ethyl]benzoic acid methyl ester; m.p. (C-I) 34.2° C.

p-[2-(trans-4-propylcyclohexyl)-1-ethyl]benzoic acid methyl ester; m.p. (C-I) 38.3° C., cl.p. (N-I) 37.7° C.

p-[2-(trans-4-butylcyclohexyl)-1-ethyl]benzoic acid methyl ester; m.p. (C-I) 39.6° C., cl.p. (N-I) 32° C.

p-[2-(trans-4-heptylcyclohexyl)-1-ethyl]benzoic acid methyl ester; m.p. (C-N) 33.5° C., cl.p. (N-I) 53° C.

We claim:

1. A compound of the formula

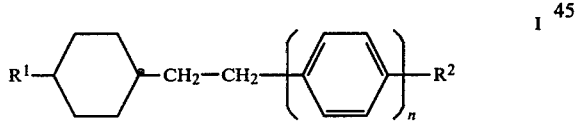

I wherein $R^2$ is $-R^3$, $-OR^3$, $-CO-R^3$, $-CO-OR^3$ or $-O-CO-R^3$, $R^1$ and $R^3$ each are straight-chain alkyl of 1 to 12 carbon atoms and n is 1 or 2.

2. The compound of claim 1 wherein $R^2$ is $-R^3$, $-OR^3$ or $-CO-OR^3$.

3. The compound of claim 2 wherein $R^2$ is $-R^3$ or $-OR^3$.

4. The compound of claim 1 wherein n is 1.

5. The compound of claim 1 wherein $R^3$ is straight-chain alkyl of 1 to 10 carbon atoms.

6. The compound of claim 5 wherein $R^3$ is straight-chain alkyl of 1 to 7 carbon atoms.

7. The compound of claim 1 wherein $R^1$ is straight-chain alkyl of 2 to 10 carbon atoms.

8. The compound of claim 7 wherein $R^1$ is straight-chain alkyl of 3 to 7 carbon atoms.

9. The compound of claim 1 wherein $R^1$ is straight-chain alkyl of 3 to 7 carbon atoms, $R^2$ is $-R^3$ or $-OR^3$, $R^3$ is straight-chain alkyl of 1 to 7 carbon atoms and n is 1.

10. A liquid crystalline mixture comprising at least two components at least one of which is a compound of the formula

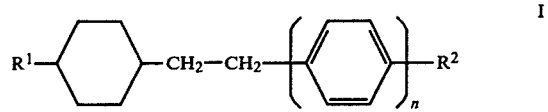

I wherein $R^2$ is $-R^3$, $-OR^3$, $-CO-R^3$, $-CO-OR^3$ or $-O-CO-R^3$, $R^1$ and $R^3$ each are straight-chain alkyl of 1 to 12 carbon atoms and n is 1 or 2.

11. The liquid crystalline mixture of claim 10 wherein the other component comprises one or more compounds selected from the group consisting of:

a compound of the formula

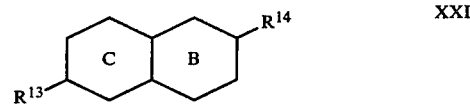

XXI wherein ring C is saturated; ring B is saturated or aromatic; $R^{13}$ is straight-chain alkyl or alkoxy of 1 to 11 carbon atoms; $R^{14}$ is cyano, straight-chain alkyl of 1 to 11 carbon atoms or an ester of the formula

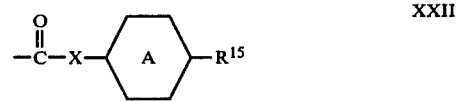

XXII wherein ring A is either aromatic and X is oxygen or sulphur and $R^{15}$ is cyano or straight-chain alkyl or alkoxy of 1 to 10 carbon atoms, or ring A is trans-1,4-disubstituted cyclohexane and X is oxygen and $R^{15}$ is cyano or a straight-chain alkyl group of 1 to 10 carbon atoms;

with the proviso that when ring B is saturated, it is trans-linked with ring C; with the additional proviso that when ring B is saturated, $R^{14}$ may also be straight-chain alkoxy of 1 to 11 carbon atoms; and with the further proviso that the total number of carbon atoms in the alkyl and alkoxy groups within Compound XXI is at most 12;

a compound of the formula

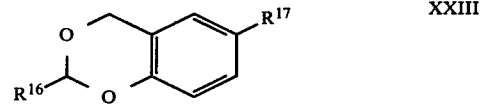

XXIII wherein $R^{16}$ is straight-chain alkyl of 1 to 11 carbon atoms; $R^{17}$ is cyano, straight-chain alkyl of 1 to 11 carbon atoms or ester XXII hereinbefore in which X, A and $R^{15}$ are as above; with the proviso that the total number of carbon atoms in the alkyl and alkoxy groups within Compound XXIII is at most 12;

a compound of the formula

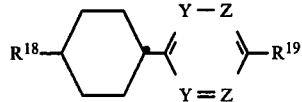

XXIV wherein Y is nitrogen and Z is =CH—, or Z is nitrogen and Y is =CH—; $R^{18}$ is alkyl and $R^{19}$ is cyano, alkyl, p-alkylphenyl or trans-4-alkylcyclohexyl; where each alkyl denotes either a straight-chain alkyl group of 1 to 12 carbon atoms or a branched-chain alkyl group of the formula $C_2H_5—CH(CH_3)—(CH_2)—_m$, m is 1, 2 or 3; with the proviso that the compound contains at most only one of said branched-chain alkyl group and with the further proviso that the sum of the carbon atoms in all of the alkyl groups within Compound XXIV is at most 14; and a compound of the formula

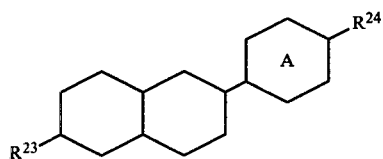

XXXVIII wherein ring A is aromatic or a trans-1,4-disubstituted cyclohexane ring; $R^{24}$ is methyl, —CH$_2$R', —OR', —CO—R', —CN, —COOH, —CO—OR', —CO—SR' or —O—CO—R'; $R^{23}$ is hydrogen, methyl, —CH$_2$R, —OR or —CH$_2$OR, or when $R^{24}$ is methyl, —CH$_2$R', —OR' or —CO—R', $R^{23}$ also can be —CN, —COOH, —CO—OR, —CO—SR or —O—CO—R; R and R' each are alkyl; and $R^{23}$ and $R^{24}$ each have up to 12 carbon atoms and together have at most 14 carbon atoms.

12. The liquid crystalline mixture of claim 10 wherein the other component comprises one or more compounds selected from the group consisting of:

a compound of the formula

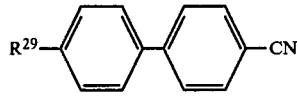

XXXXIV wherein $R^{29}$ is straight-chain alkyl or alkoxy of 2 to 7 carbon atoms;

a compound of the formula

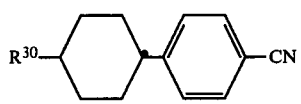

VL wherein $R^{30}$ is straight-chain alkyl of 3 to 7 carbon atoms;

a compound of the formula

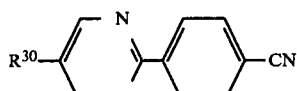

VLI wherein $R^{30}$ is as above, a compound of the formula

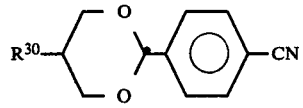

VLII wherein $R^{30}$ is as above;

a compound of the formula

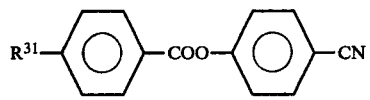

VLIII wherein $R^{31}$ is straight-chain alkyl of 2 to 7 carbon atoms;

a compound of the formula

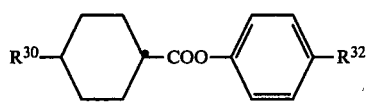

IL wherein $R^{30}$ is as above and $R^{32}$ is cyano or straight-chain alkoxy of 1 to 3 carbon atoms;

a compound of the formula

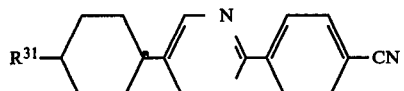

L wherein $R^{31}$ is as above; and a compound of the formula

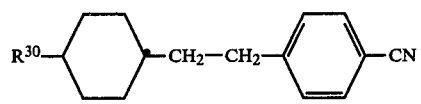

LI wherein $R^{30}$ is as above.

13. In accordance with claim 9, 2-(trans-4-pentylcyclohexyl)-1-(p-ethoxyphenyl)ethane.

14. In accordance with claim 9, 2-(trans-4-propylcyclohexyl)-1-(p-ethoxyphenyl)ethane.

15. In accordance with claim 9, 2-(trans-4-propylcyclohexyl)-1-(p-butyloxyphenyl)ethane.

16. In accordance with claim 9, 2-(trans-4-pentylcyclohexyl)-1-(p-butyloxyphenyl)ethane.

17. In accordance with claim 9, 2-(trans-4-butylcyclohexyl)-1-(p-ethoxyphenyl)ethane.

18. In accordance with claim 9, 2-(trans-4-pentylcyclohexyl)-1-(p-propylphenyl)ethane.

19. In accordance with claim 9, 2-(trans-4-heptylcyclohexyl)-1-(p-butylphenyl)ethane.

20. An electro-optical cell comprising (a) two plate means;

(b) liquid crystal means disposed between the two plate means and including a compound of the formula:

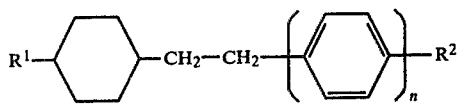
wherein $R^2$ is $-R^3$, $-OR^3$, $-CO-R^3$, $-CO-OR^3$ or $-O-CO-R^3$, $R^1$ and $R^3$ each are straight-chain alkyl of 1 to 12 carbon atoms and n is 1 or 2; and
(c) means for applying an electric potential to said plate means.
* * * * *